United States Patent
Yoo et al.

(10) Patent No.: US 11,332,475 B2
(45) Date of Patent: May 17, 2022

(54) OPTICALLY ACTIVE PYRANOCHROMENYL PHENOL DERIVATIVE AND PHARMACEUTICAL COMPOSITION COMPRISING SAME

(71) Applicant: GLACEUM, INC., Suwon-si (KR)

(72) Inventors: Sang Ku Yoo, Suwon-si (KR); Jin Wook Chung, Seoul (KR); In Geun Jo, Cheonan-si (KR); Ji Young Kim, Seoul (KR); Jeong Ho Im, Gwangju-si (KR); Ku Suk Kang, Yongin-si (KR); Jin Young Kim, Suwon-si (KR)

(73) Assignee: GLACEUM, INC.

( * ) Notice: Subject to any disclaimer, the term of this patent is extended or adjusted under 35 U.S.C. 154(b) by 0 days.

(21) Appl. No.: 17/114,584

(22) Filed: Dec. 8, 2020

(65) Prior Publication Data
US 2021/0094967 A1 Apr. 1, 2021

Related U.S. Application Data

(63) Continuation of application No. 16/313,777, filed as application No. PCT/KR2017/006863 on Jun. 29, 2017, now abandoned.

(30) Foreign Application Priority Data

Jun. 29, 2016 (KR) .................. 10-2016-0081674

(51) Int. Cl.
*A61K 31/353* (2006.01)
*C07D 493/04* (2006.01)
*A61K 31/352* (2006.01)
*A61P 3/04* (2006.01)
*C07B 57/00* (2006.01)

(52) U.S. Cl.
CPC .......... *C07D 493/04* (2013.01); *A61K 31/352* (2013.01); *A61K 31/353* (2013.01);
(Continued)

(58) Field of Classification Search
CPC .. C07D 493/04; A61K 31/352; A61K 31/353; A61P 3/04; C07B 57/00; C07B 2200/07; Y10S 514/866; Y10S 514/909
(Continued)

(56) References Cited

U.S. PATENT DOCUMENTS 9,783,551 B2 * 10/2017 Yoo .................. A61P 29/00
2005/0014819 A1 1/2005 Mae et al.
(Continued)

FOREIGN PATENT DOCUMENTS

CA 2929001 7/2015
CN 105849111 A 8/2016
(Continued)

OTHER PUBLICATIONS

Fanie R. van Heerden et al Structure and Synthesis of some complex Pyranoisoflavonoids from Bark of *Dalbergia nitidula* Welw.ex Bak. (Year: 1977).*

(Continued)

*Primary Examiner* — Taylor V Oh
(74) *Attorney, Agent, or Firm* — Myers Bigel, P.A.

(57) ABSTRACT

The present invention relates to pyranochromenylphenol derivatives having different efficacies depending on the direction of optical activity and a pharmaceutical composition including the same, and in the pyranochromenylphenol derivatives, an R-enantiomer has excellent anti-diabetic efficacy by suppressing a rise in blood sugar and an S-enantiomer has excellent anti-obesity efficacy by suppressing an increase in body weight.

13 Claims, 7 Drawing Sheets

(52) U.S. Cl.
    CPC ............. *A61P 3/04* (2018.01); *C07B 57/00* (2013.01); *C07B 2200/07* (2013.01)
(58) Field of Classification Search
    USPC ........................................................ 514/454
    See application file for complete search history.

(56) References Cited

U.S. PATENT DOCUMENTS

| | | | |
|---|---|---|---|
| 2007/0098761 | A1 | 5/2007 | Arai et al. |
| 2016/0272650 | A1 | 9/2016 | Yoo et al. |

FOREIGN PATENT DOCUMENTS

| | | | |
|---|---|---|---|
| EP | 3524609 | 8/2019 | |
| KR | 1020050035142 | 4/2005 | |
| KR | 1020060119706 | 11/2006 | |
| KR | 1020070052211 | 5/2007 | |
| KR | 1020150075030 | 7/2015 | |
| WO | 2007058480 | 5/2007 | |
| WO | 2015099392 | 7/2015 | |
| WO | WO-2015099392 A1 * | 7/2015 | ............. A61P 3/00 |

OTHER PUBLICATIONS

Nadin Shukor Flavonoids: Evidence for Inhibitory Effects against obesity and their possible mechanism of Action. (Year: 2016).*

English language translation of International Search Report corresponding to International Patent Application No. PCT/KR2017/006863 dated Sep. 21, 2017 (2 pages).

Extended European Search Report corresponding to EP 17820539.9, dated Jan. 24, 2020 (7 pages).

Japanese Office Action corresponding to JP 2018-569103, dated Oct. 28, 2019 (7 pp including English translation).

Mane, S. "Racemic drug resolution: a comprehensive guide" Analytical Methods, 8(42):7567-7586 (2016).

New Zealand Office Action corresponding to Application No. 749461, dated Aug. 26, 2019 (4 pp).

Chhabra, et al., "A review of drug isomerism and its significance" International Journal of Applied and Basic Medical Research 3(1):16-18 (2013).

George, et al., "Lean diabetes mellitus: An emerging entity in the era of obesity" World Journal of Diabetes 6(4):613-620 (2015).

Islam, Mohamed, et al., "Pharmacological Importance of Sterochemical Resolution of Enantiomeric Drugs" (Year: 1997).

Jirawattanapong, et al., "Synthesis of Glabridin Derivatives as Tyrosinase Inhibitors" Archives of Pharmacal Research 32(5):647-654 (2009).

Van Heerden, et al., "Structure and Synthesis of Some Complex Pyranoisoflavonoids from the Bark of *Dalbergia nitidula* Welw. ex Bak." Journal of Chemical Society, Perkin Transactions 1, 137-145 (1978).

Yamanaka, et al., "Chemistry Reviews Separation of Optical Isomers" Chemistry Reviews, 6: pp. 8, 9, 123, 124, 212, 213 (1999) (English translation of pp. 8, 9, 123, 124, 212, 213 included).

* cited by examiner

OPTICALLY ACTIVE PYRANOCHROMENYL PHENOL DERIVATIVE AND PHARMACEUTICAL COMPOSITION COMPRISING SAME

CROSS REFERENCE TO RELATED APPLICATIONS

This application is a Continuation of U.S. patent application Ser. No. 16/313,777, filed Dec. 27, 2018, which is a 35 U.S.C. § 371 national stage application of PCT International Application No. PCT/KR20171006863, filed Jun. 29, 2017, which claims priority from Korean Patent Application No. 10-2016-0081674, filed Jun. 29, 2016, the contents of which are incorporated herein in their entireties by reference. The above-referenced PCT International Application was published in the Korean language as International Publication No. WO 2018/004263 on Jan. 4, 2018.

TECHNICAL FIELD

The present invention relates to pyranochromenylphenol derivatives having different efficacies depending on the direction of optical activity and a pharmaceutical composition including the same, and to an R-enantiomer having excellent anti-diabetic efficacy and an S-enantiomer having excellent anti-obesity efficacy and a pharmaceutical composition including each of the enantiomers.

BACKGROUND ART

Obesity, which about 30 to 40% of modern people have, is defined as a state in which excessive fat tissues are accumulated in the body, and obesity occurs when excessive energy is accumulated due to imbalance of energy supply in the human body. Due to improvement in the standard of living resulting from the recent economic development, frequent ingestion of instant food products and dietary habits of consumption of large amounts of meat lead to a rapid increase in obesity ratio.

Meanwhile, diabetes is one of the metabolic disorders which show a phenomenon in which the amount of insulin secreted is insufficient or insulin does not perform normal functions, and diabetes is characterized by hyperglycemia in which the concentration of glucose in blood is increased, and is defined as a disease in which various syndromes and symptoms are shown due to hyperglycemia, and glucose is released in the urine. In order to treat diabetes and prevent complications thereof, it is the most important to adjust blood sugar, and there are glycated hemoglobin (HbA1C), and the like as a primary efficacy endpoint which is involved in the adjustment of blood sugar.

Since obesity is caused by imbalance of energy when more excessive nutrients are absorbed than the amount of energy consumed for a long period of time, it is known that obesity increases not only the attack rate of diabetes, fatty liver, dyslipidemia, and the like, but also the attack rate of sexual dysfunction, arthritis, cardiovascular diseases, obstructive sleep apnea, and the like, and is responsible for cholelithiasis and several cancers. For this reason, the World Health Organization (WHO) stipulates that obesity is responsible for causing various metabolic diseases (adult diseases), and obesity is also responsible for diabetes, and conversely, diabetic patients evolve into an obese state, and the like due to insulin resistance, so that obesity and diabetes can be said to be diseases affecting each other.

However, for the correlation between diabetes and obesity, it is estimated that the Europeans and the Africans have a correlation of approximately 60% and the Asians such as Koreans, Chinese, and Japanese have a correlation of approximately 30%, and there are a considerable number of diabetic patients with normal body weight or lean body build for various reasons (Non-Patent Document 1). Further, since the target and indicator of a therapeutic agent for obesity is to reduce the body weight, and the target and indicator of a therapeutic agent for diabetes is to adjust blood sugar, the targets and therapeutic methods of the two diseases are different from each other in terms of the adjustment of blood sugar.

Glabridin is a compound found from *Glycyrrhiza glabra* extract, and is known to have whitening activity by suppressing the activity of tyrosinase during the synthetic process of melanin, and to help alleviate gastroenteric disorders. Recently, it was confirmed that glabridin is effective for metabolic syndromes including hyperlipidemia, fatty liver, impaired glucose metabolism, diabetes, and obesity, and has anti-inflammatory actions, anti-cancer actions, and the like (Patent Document 1). However, inspite of useful medicinal efficacy, glabridin is easily broken down by sunlight, moisture, acidity, basicity, oxygen, heat, and the like due to low chemical stability, so that it is very difficult to develop a product actually utilizing glabridin (Non-Patent Document 2).

For the aforementioned reasons, the inventors of the present invention suggested a new direction for treating various metabolic diseases and inflammatory diseases by synthesizing a new pyranochromenylphenol derivative of the following Chemical Formula (I), which is stable under various physical conditions while maintaining or improving the medicinal efficacy of glabridin (Patent Document 2).

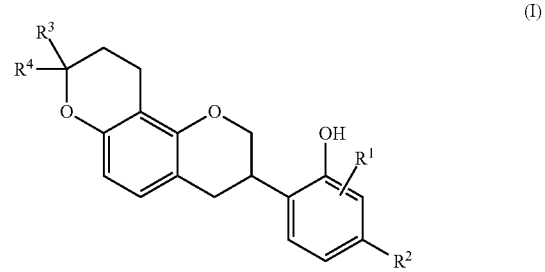

(I)

In the chemical formula, $R^1$ is a hydrogen atom, methyl, methoxy, or a halogen atom;

$R^2$ is a hydrogen atom; a substituted or unsubstituted straight or branched $C_1$ to $C_6$ alkyl group; a halogen atom; a substituted or unsubstituted straight or branched $C_1$ to $c_6$ alkoxy group; or a substituted or unsubstituted straight or branched $C_1$ to $C_4$ thioalkyl group;

$R^3$ and $R^4$ are each independently a hydrogen atom or a $C_1$ to $C_2$ alkyl group; and in the case of the substituted alkyl, the substituted alkoxy, and the substituted thioalkyl, the substituent is a halogen atom, a straight or branched $C_1$ to $c_5$ alkyl group, a straight or branched $C_1$ to $c_5$ alkoxy group or a straight or branched $C_1$ to $c_3$ thioalkyl group.

In the Patent Document 2, the compound of Chemical Formula (I) has one asymmetric carbon, and the present invention is intended to suggest that in the specific derivatives of these compounds, an R-enantiomer has an excellent effect in treating diabetes and an S-enantiomer has an excellent effect in treating obesity.

REFERENCES OF THE RELATED ART

Patent Documents (Patent Document 1) International Publication No. WO 07/058480
(Patent Document 2) Korean Patent Application Laid-Open No. 10-2015-0075030

Non-Patent Documents (Non-Patent Document 1) "Lean diabetes mellitus: An emerging entity in the era of obesity", George A. M., et al., World 3 Diabetes, 2015 May 15; 6(4): 613-620
(Non-Patent Document 2) M. Ao, Natural Product Communication 5 (2010), 1907~1912.

DETAILED DESCRIPTION OF THE INVENTION

Technical Problem

An aspect of the present invention is to provide an optically active pyranochromenylphenol derivative which has excellent anti-diabetic efficacy and is chemically stable, and a pharmaceutical composition including the same.

Another aspect of the present invention is to provide an optically active pyranochromenylphenol derivative which has excellent anti-obesity efficacy and is chemically stable, and a pharmaceutical composition including the same.

Technical Solution

An aspect of the present invention provides an optically active pyranochromenylphenol compound of the following Chemical Formula 1, a pharmaceutically acceptable salt, or a solvate thereof, and a pharmaceutical composition including the same:

[Chemical Formula 1]

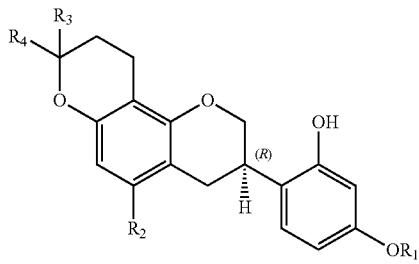

wherein
$R_1$ is a straight or branched $C_1$ to $C_6$ alkyl group unsubstituted or substituted by a straight or branched $C_1$ to $C_5$ alkyl group, a halogen atom, or a $C_1$ to $C_5$ thioalkyl group;
$R_2$ is a hydrogen atom, or a $C_1$ to $C_2$ alkyl group, or a $C_1$ to $C_2$ alkoxy group; and
$R_3$ and R are each independently a hydrogen atom or a $C_1$ to $C_2$ alkyl group.

Another aspect of the present invention provides an optically active pyranochromenylphenol compound of the following Chemical Formula 2, a pharmaceutically acceptable salt, or a solvate thereof, and a pharmaceutical composition including the same:

[Chemical Formula 2]

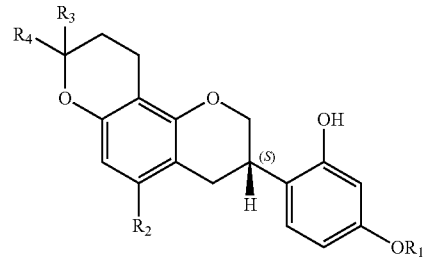

wherein
$R_1$ is a straight or branched $C_1$ to $C_6$ alkyl group unsubstituted or substituted by a straight or branched $C_1$ to $C_5$ alkyl group, a halogen atom, or a $C_1$ to $C_5$ thioalkyl group;
$R_2$ is a hydrogen atom, or a $C_1$ to $C_2$ alkyl group, or a $C_1$ to $C_2$ alkoxy group; and
$R_3$ and $R_4$ are each independently a hydrogen atom or a $C_1$ to $C_2$ alkyl group.

Advantageous Effects

In the optically active pyranochromenylphenol derivatives of the present invention, an R-enantiomer is more chemically stable than glabridin and has excellent anti-diabetic efficacy, and an S-enantiomer has excellent anti-obesity efficacy and is more chemically stable than glabridin.

MODE FOR INVENTION

Figure 1:
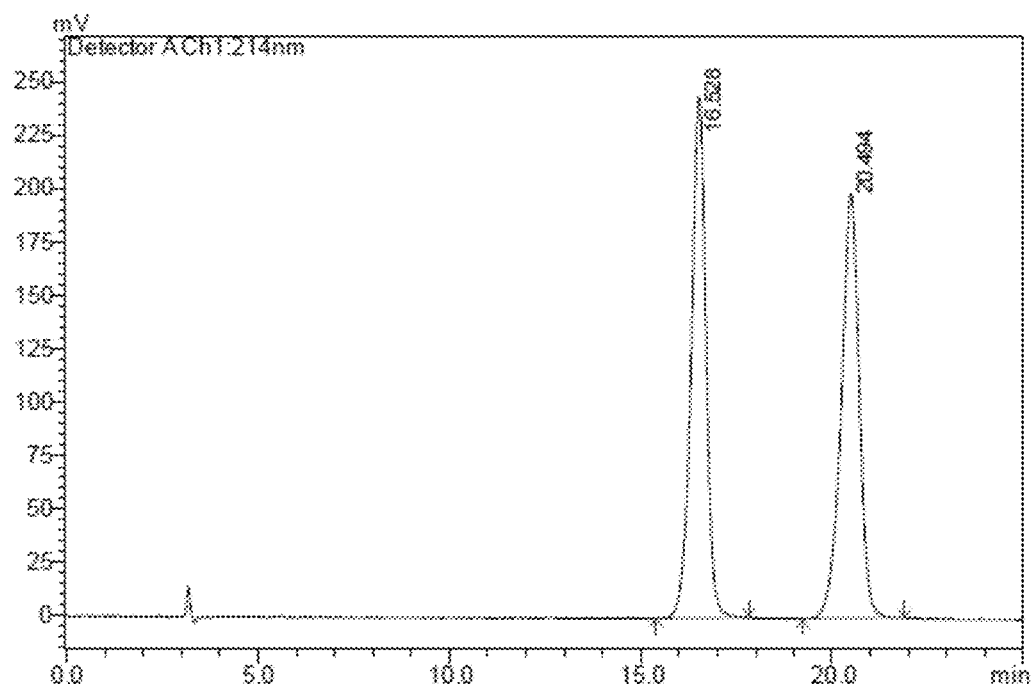
FIG. 1 is a column chromatogram of optically active pyranochromenylphenol compounds 2a and 2b prepared in Example 1 of the present invention.

Hereinafter, the present invention will be described in more detail.

All the technical terms used in the present invention are used in the same sense as those generally understood by the person skilled in the related art of the present invention, unless otherwise defined. Further, in the present specification, a preferred method or sample is described, but those similar or equivalent thereto also fall within the scope of the present invention. The contents of all the publications described as a reference document in the present specification are incorporated by reference into the present specification.

According to an aspect of the present invention, provided is an optically active pyranochromenylphenol compound of the following Chemical Formula 1, a pharmaceutically acceptable salt, or a solvate thereof:

[Chemical Formula 1]

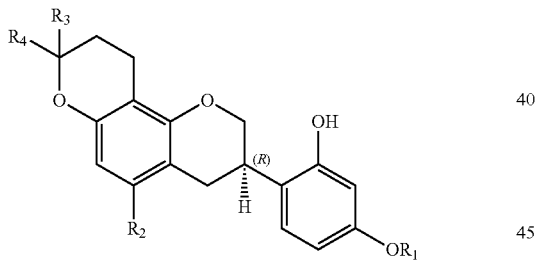

wherein $R_1$ is a straight or branched $C_1$ to $C_6$ alkyl group unsubstituted or substituted by a straight or branched $C_1$ to $C_5$ alkyl group, a halogen atom, or a $C_1$ to $C_5$ thioalkyl group;

$R_2$ is a hydrogen atom, or a $C_1$ to $C_2$ alkyl group, or a $C_1$ to $C_2$ alkoxy group; and $R_3$ and $R_4$ are each independently a hydrogen atom or a $C_1$ to $C_2$ alkyl group.

According to an exemplary embodiment of the present invention, in Chemical Formula 1, $R_1$ may be methyl, ethyl, n-propyl, isopropyl, n-butyl, 2-methylpropyl, n-pentyl, 2-methylbutyl, 3-methylbutyl, 2-ethylpropyl, n-hexyl, 2-methylpentyl, 3-methylpentyl, 4-methylpentyl, or 2-ethylbutyl, $R_2$ may be a hydrogen atom, and $R_3$ and $R_4$ may be each methyl.

According to an exemplary embodiment, the optically active pyranochromenylphenol compound of Chemical Formula 1 may be any one of the following compounds:

<Compound 1a>

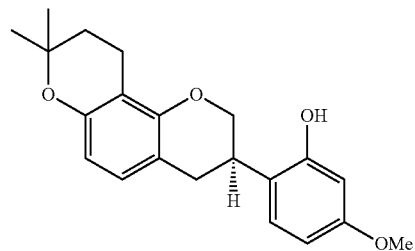

<Compound 2a>

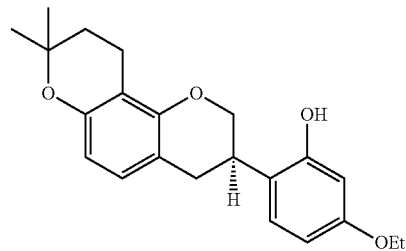

<Compound 3a>

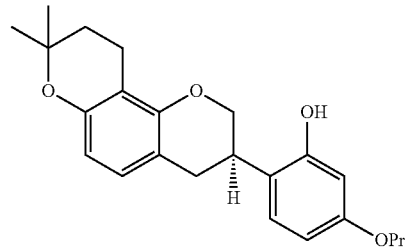

<Compound 4a>

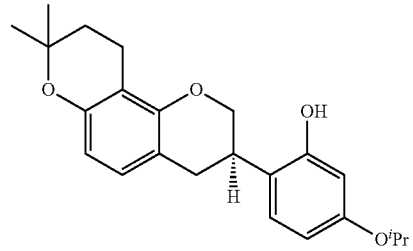

<Compound 5a>

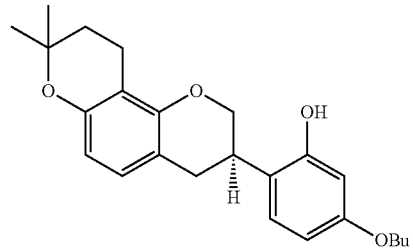

<Compound 6a>

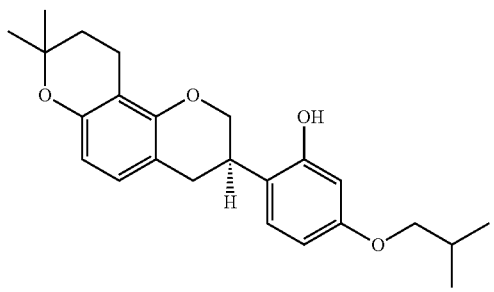

<Compound 7a>

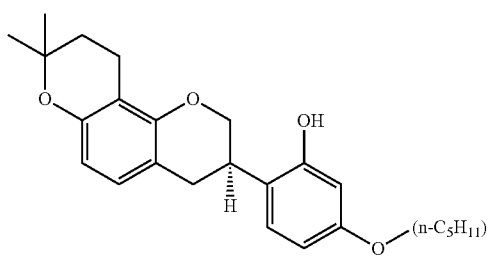

<Compound 8a>

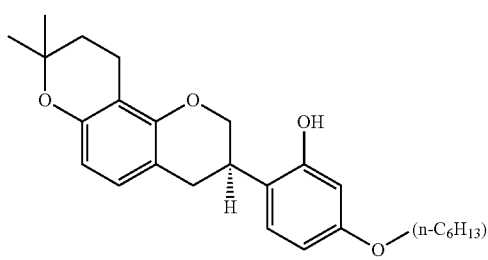

<Compound 9a>

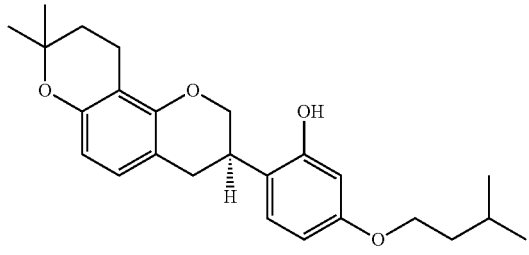

According to an exemplary embodiment of the present invention, the optically active pyranochromenylphenol compound of Chemical Formula (I) has an excellent effect of preventing and treating diabetes due to the excellent ability to adjust blood sugar, and simultaneously, is excellent in terms of chemical stability.

According to another aspect of the present invention, provided is an optically active pyranochromenylphenol compound of the following Chemical Formula 2, a pharmaceutically acceptable salt, or a solvate thereof:

[Chemical Formula 2]

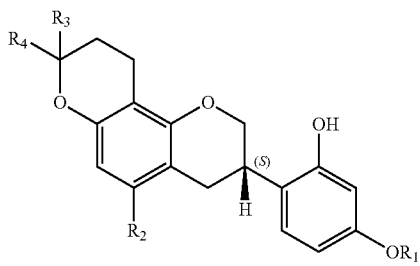

wherein
$R_1$ is a straight or branched $C_1$ to $C_6$ alkyl group unsubstituted or substituted by a straight or branched $C_1$ to $C_5$ alkyl group, a halogen atom, or a $C_1$ to $C_5$ thioalkyl group;
$R_2$ is a hydrogen atom, or a $C_1$ to $C_2$ alkyl group, or a $C_1$ to $C_2$ alkoxy group; and
$R_3$ and $R_4$ are each independently a hydrogen atom or a $C_1$ to $C_2$ alkyl group.

According to an exemplary embodiment of the present invention, in Chemical Formula 2, $R_1$ may be methyl, ethyl, n-propyl, isopropyl, n-butyl, 2-methylpropyl, n-pentyl, 2-methylbutyl, 3-methylbutyl, 2-ethylpropyl, n-hexyl, 2-methylpentyl, 3-methylpentyl, 4-methylpentyl, or 2-ethylbutyl, $R_2$ may be a hydrogen atom, and $R_3$ and $R_4$ may be each methyl.

According to an exemplary embodiment, the optically active pyranochromenylphenol compound of Chemical Formula 2 may be any one of the following compounds:

<Compound 1b>

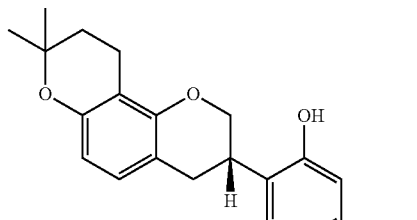

<Compound 2b>

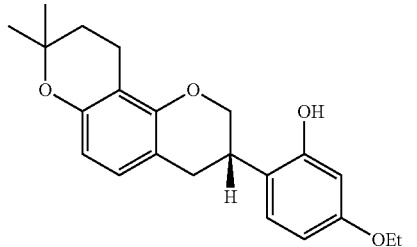

<Compound 3b>

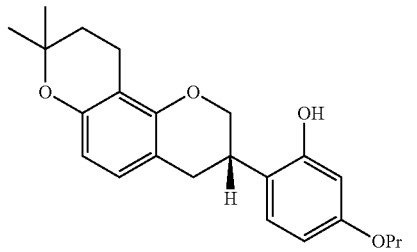

<Compound 4b>

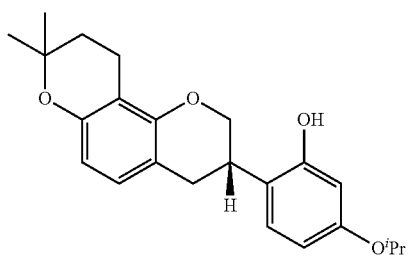

<Compound 9b>

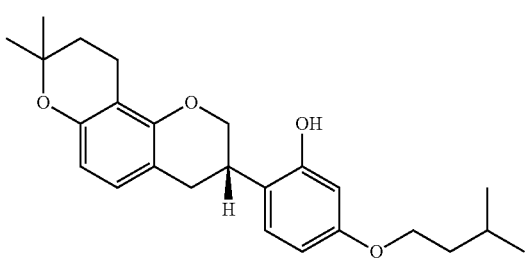

<Compound 5b>

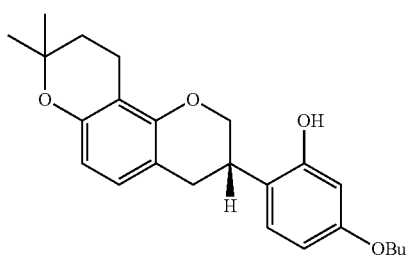

<Compound 6b>

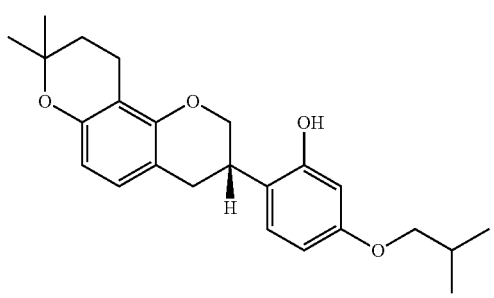

<Compound 7b>

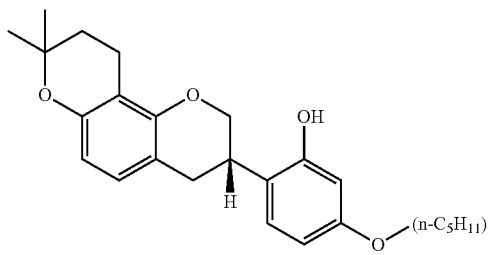

<Compound 8b>

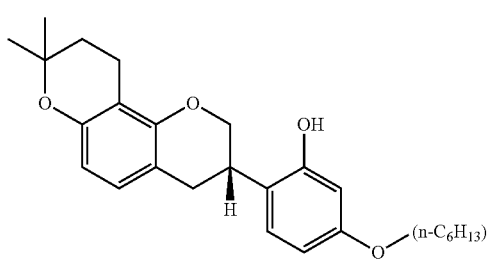

According to an exemplary embodiment of the present invention, the optically active pyranochromenylphenol compound of Chemical Formula 2 has an excellent effect of preventing and treating obesity by suppressing an increase in body weight and simultaneously, is excellent in terms of chemical stability.

According to an exemplary embodiment of the present invention, the pharmaceutically acceptable salt may be present as an acid addition salt because the compound of Chemical Formula 1 or the compound of Chemical Formula 2 forms a salt with a free acid. The compound of Chemical Formula 1 or the compound of Chemical Formula 2 may form a pharmaceutically acceptable acid addition salt according to the typical method publicly known in the art. An organic acid or an inorganic acid may be used as the free acid, hydrochloric acid, bromic acid, sulfuric acid, or phosphoric acid, and the like may be used as the inorganic acid, and citric acid, acetic acid, lactic acid, tartariac acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid or aspartic acid, and the like as the organic acid.

The pharmaceutically acceptable salt may be present as an inorganic salt of the compound of Chemical Formula 1 or the compound of Chemical Formula 2. The compound of Chemical Formula 1 or the compound of Chemical Formula 2 may form a pharmaceutically acceptable inorganic salt according to the typical method publicly known in the art. Examples of the inorganic salt include salts with aluminum, ammonium, calcium, copper, iron, lithium, magnesium, manganese, potassium, sodium, or zinc, but are not limited thereto, and ammonium, calcium, magnesium, potassium, or sodium salts are preferred.

Further, according to an exemplary embodiment of the present invention, the compound of Chemical Formula 1 or the compound of Chemical Formula 2 may include not only pharmaceutically acceptable salts, but also all the salts and solvates including hydrates, which may be prepared by typical methods.

A method of preparing the compound of Chemical Formula 1 or the compound of Chemical Formula 2 is not particularly limited, but the compound of Chemical Formula 1 or the compound of Chemical Formula 2 may be prepared based on the preparation method disclosed in Korean Patent Application Laid-Open No. 10-2015-0075030 (Patent Document 2). That is, it is possible to obtain an R-enantiomer and an S-enantiomer, which are optically active pyranochromenylphenol compounds, by separating a racemic compound of the pyranochromenylphenol compound prepared by the method disclosed in the document by means of a separation method such as column chromatography.

According to another aspect of the present invention, provided is a pharmaceutical composition for preventing or treating diabetes, including an optically active pyranochromenylphenol compound of the following Chemical Formula 1, a pharmaceutically acceptable salt, or a solvate thereof:

[Chemical Formula 1]

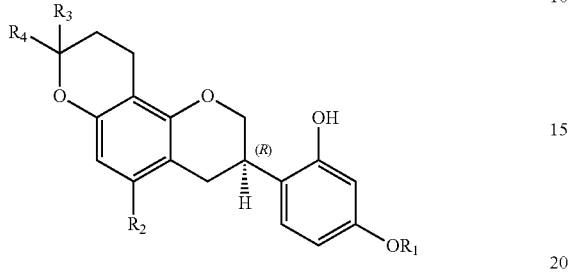

wherein $R_1$ is a straight or branched $C_1$ to $C_6$ alkyl group unsubstituted or substituted by a straight or branched $C_1$ to $C_5$ alkyl group, a halogen atom, or a $C_1$ to $C_5$ thioalkyl group;

$R_2$ is a hydrogen atom, or a $C_1$ to $C_2$ alkyl group, or a $C_1$ to $C_2$ alkoxy group; and $R_3$ and $R_4$ are each independently a hydrogen atom or a $C_1$ to $C_2$ alkyl group.

According to an exemplary embodiment of the present invention, the optically active pyranochromenylphenol compound of Chemical Formula 1 may be any one of the following compounds:

<Compound 1a>

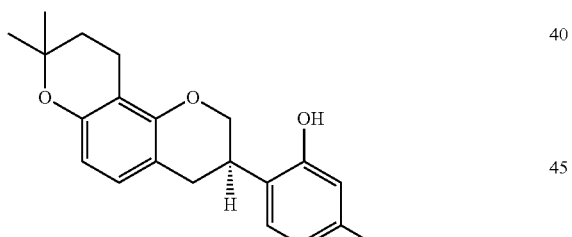

<Compound 2a>

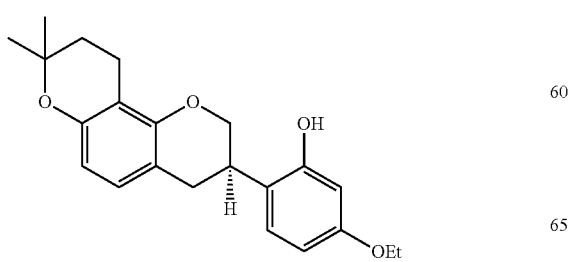

<Compound 3a>

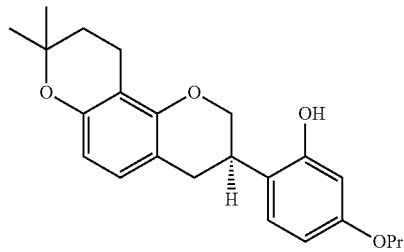

<Compound 4a>

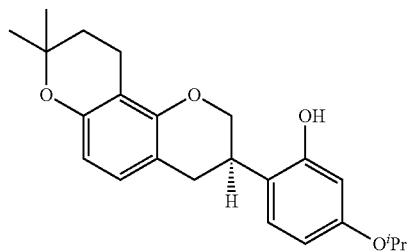

<Compound 5a>

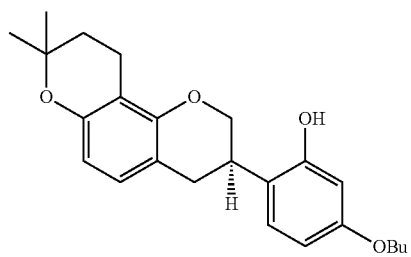

<Compound 6a>

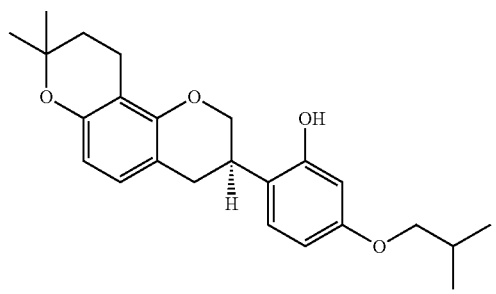

<Compound 7a>

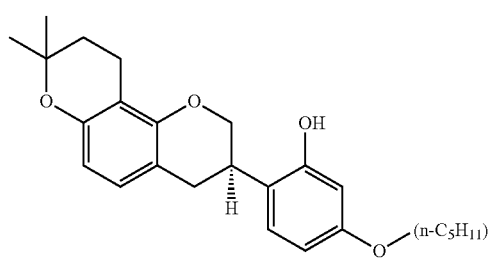

<Compound 8a>

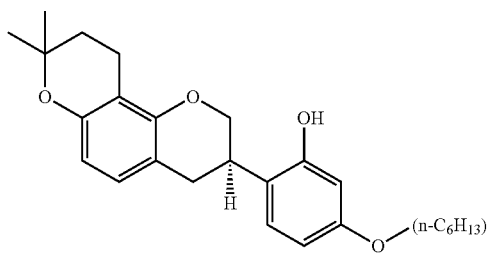

<Compound 1b>

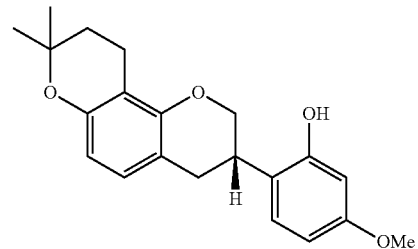

<Compound 9a>

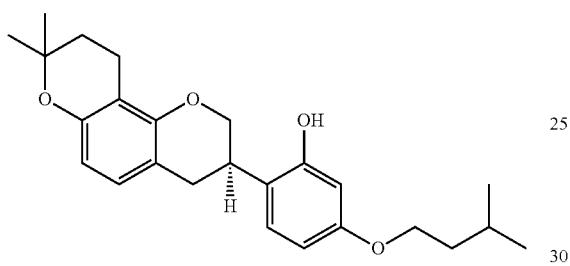

<Compound 2b>

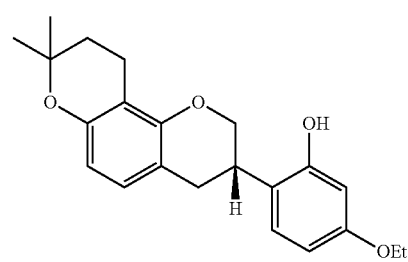

According to still another aspect of the present invention, provided is a pharmaceutical composition for preventing or treating obesity, including an optically active pyranochromenylphenol compound of the following Chemical Formula 2, a pharmaceutically acceptable salt, or a solvate thereof:

[Chemical Formula 2]

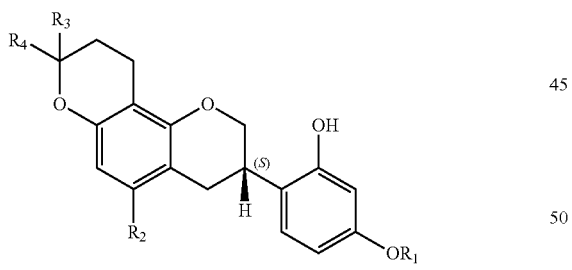

wherein

R₁ is a straight or branched $C_1$ to $C_6$ alkyl group unsubstituted or substituted by a straight or branched $C_1$ to $C_5$ alkyl group, a halogen atom, or a $C_1$ to $C_5$ thioalkyl group;

R₂ is a hydrogen atom, or a $C_1$ to $C_2$ alkyl group, or a $C_1$ to $C_2$ alkoxy group; and R₃ and R₄ are each independently a hydrogen atom or a $C_1$ to $C_2$ alkyl group.

According to an exemplary embodiment of the present invention, the optically active pyranochromenylphenol compound of Chemical Formula 2 may be any one of the following compounds:

<Compound 3b>

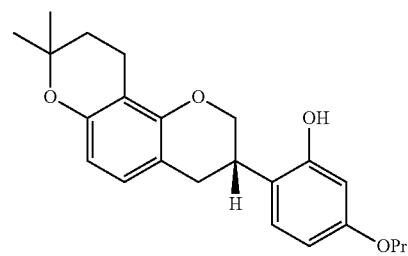

<Compound 4b>

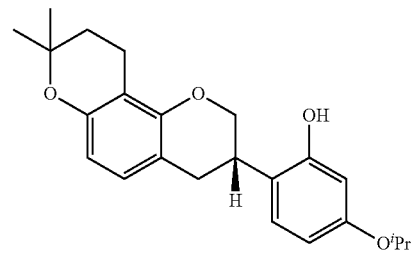

<Compound 5b>

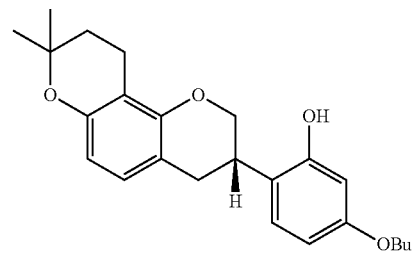

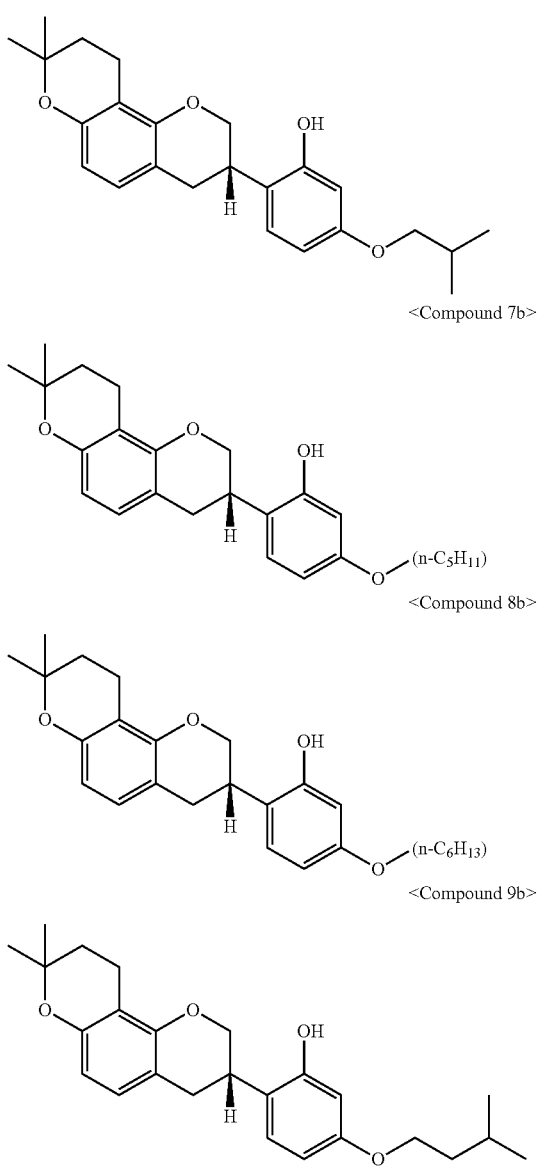

<Compound 6b>

<Compound 7b>

<Compound 8b>

<Compound 9b>

The pharmaceutical composition may be formulated into a typical pharmaceutical dosage form publicly known in the art. The dosage form includes orally administered preparations, injection preparations, suppositories, percutaneous administration preparations, and nasal administration preparations, but may also be administered by being formulated into any dosage form which is not limited thereto, but may be preferably formulated into a preparation for oral administration and an injection preparation.

When the pharmaceutical composition is formulated into each dosage form, the dosage form may be prepared by adding a pharmaceutically acceptable carrier required for the preparation of each dosage form. In the present specification, the term "pharmaceutically acceptable carrier" is used to refer to any constituent ingredient excluding a pharmaceutically active ingredient. The "pharmaceutically acceptable" means the properties that do not cause any pharmaceutically undesirable change via interaction with other ingredients present in a composition (for example, interaction between carriers or interaction between the pharmaceutically active ingredient and a carrier). Selection of the pharmaceutically acceptable carrier may vary depending on factors such as the properties and the administration method of a particular dosage form, and the effects of the carrier on solubility and stability of the dosage form.

According to an exemplary embodiment of the present invention, a pharmaceutically acceptable carrier included in a pharmaceutical composition for oral administration may be one selected from a diluent, a binder, a glidant (or a lubricant), a disintegrant, a stabilizer, a solubilizing agent, a sweetening agent, a coloring agent, and a flavoring agent, but is not limited thereto.

A diluent refers to any excipient that is added to increase the volume of a composition to formulate the composition into a dosage form with an appropriate size. As the diluent, it is possible to use starch (for example, potato starch, corn starch, wheat starch, pregelatinized starch), microcrystalline cellulose (for example, low-hydration microcrystalline cellulose), lactose (for example, lactose monohydrate, anhydrous lactose, spray lactose), glucose, sorbitol, mannitol, sucrose, alginate, alkaline earth metal salts, clay, polyethylene glycol, dicalcium phosphate, anhydrous calcium hydrogenphosphate, or silicon dioxide, and the like either alone or in a mixture thereof, but the diluent is not limited thereto. In the present invention, the excipient may be used within a range of 5 wt % to 50 wt % based on a total weight of the pharmaceutical composition, and may be used, for example, in an amount of 10 wt % to 35 wt % based on the total weight of the pharmaceutical composition for tableting and quality maintenance.

A binder refers to a material that is used to impart adhesiveness to materials in a powder form so as to facilitate compression of the materials and improve flowability. The binder may be one or more selected from starch, microcrystalline cellulose, highly dispersible silica, mannitol, lactose, polyethylene glycol, polyvinylpyrrolidone, cellulose derivatives (for example, hydroxypropyl methylcellulose, hydroxypropyl cellulose, or low-substituted hydroxypropyl cellulose), natural gum, synthetic gum, povidone, co-povidone, and gelatin, but is not limited thereto. In the present invention, the binder may be used in an amount of 2 wt % to 15 wt % based on a total weight of the pharmaceutical composition, and may be used, for example, in an amount of 1 wt % to 3 wt % based on the total weight of the pharmaceutical composition for tableting and quality maintenance.

A disintegrant refers to a material that is added to facilitate breakup or disintegration of a solid dosage form after being administered to a living body. As the disintegrant, it is possible to use starch such as sodium starch glycolate, corn starch, potato starch or pregelatinized starch, or modified starch, clay such as bentonite, montmorillonite or veegum, cellulose such as microcrystalline cellulose, hydroxypropyl cellulose or carboxymethyl cellulose, algins such as sodium alginate or alginic acid, a cross-linked cellulose such as croscarmellose sodium, gum such as guar gum or xanthan gum, a cross-linked polymer such as cross-linked polyvinylpyrrolidone (crospovidone), or an effervescent preparation such as sodium bicarbonate or citric acid either alone or in a mixture thereof, but the disintegrant is not limited thereto. In the present invention, the disintegrant may be used in an amount of 2 wt % to 15 wt % based on a total weight of the pharmaceutical composition, and may be used, for example, in an amount of 4 wt % to 10 wt % based on the total weight of the pharmaceutical composition for tableting and quality maintenance.

A glidant or lubricant refers to a material that performs a function of preventing cohesion of powders to a compressing system and improving flowability of granules. As the glidant, it is possible to use hard anhydrous silicic acid, talc, stearic acid, a metal salt (magnesium salt, calcium salt, or the like) of stearic acid, sodium lauryl sulfate, hydrogenated vegetable oil, sodium benzoate, sodium stearyl fumarate, glyceryl behenate, glyceryl monostearate, or polyethylene glycol either alone or in a mixture thereof, but the glidant is not limited thereto. In the present invention, the glidant may be used in an amount of 0.1 wt % to 5 wt % based on a total weight of the pharmaceutical composition, and may be used, for example, in an amount of 1 wt % to 3 wt % based on the total weight of the pharmaceutical composition for tableting and quality maintenance.

As an adsorbent, it is possible to use hydrated silicon dioxide, hard anhydrous silicic acid, colloidal silicon dioxide, magnesium aluminometasilicate, microcrystalline cellulose, lactose, or a cross-linked polyvinylpyrrolidone either alone or in a mixture thereof, but the adsorbent is not limited thereto.

A stabilizer may be one or more selected from antioxidants such as butylhydroxyanisole, butylhydroxytoluene, carotene, retinol, ascorbic acid, tocopherol, tocopherol polyethylene glycol succinic acid or propyl gallate, cyclic compounds of sugars such as cyclodextrin, carboxyethyl cyclodextrin, hydroxypropyl cyclodextrin, sulfobutyl ether or cyclodextrin, and organic acids such as phosphoric acid, lactic acid, acetic acid, citric acid, tartaric acid, succinic acid, maleic acid, fumaric acid, glycolic acid, propionic acid, gluconic acid or glucuronic acid, but is not limited thereto.

Selectively, a publicly known additive for enhancing the taste by boosting the sense of taste may be included in the pharmaceutical composition. For example, a sweetening agent such as sucralose, sucrose, fructose, erythritol, acesulfame potassium, sugar alcohol, honey, sorbitol, or aspartame may be added to more effectively mask bitterness and maintain the stability and quality of the preparation. Further, an acidifier such as citric acid or sodium citrate, a natural flavor such as Japanese apricot flavor, lemon flavor, pineapple flavor or herbal flavor, or a natural pigment such as natural fruit juice, chlorophyllin, or flavonoid may be used.

The pharmaceutical composition for oral administration may be a solid preparation, a semi-solid preparation, or a liquid preparation, for oral administration. Examples of the solid preparation for oral administration include tablets, pills, hard or soft capsules, powders, fine granules, granules, powders for reconstitution of solution or suspension, lozenges, wafers, oral strips, dragees and chewable gum, and the like, but are not limited thereto. Examples of the liquid preparation for oral administration include solution, suspension, emulsion, syrup, elixir, spirit, aromatic waters, lemonade, extract, precipitant, tincture, and oily medicine. Examples of the semi-solid preparation include aerosol, cream, gel and the like, but are not limited thereto.

The pharmaceutical composition according to the present invention may be formulated into an injection preparation, and when the composition is formulated into an injection preparation, the composition may include a non-toxic buffer solution, which is isotonic to blood, as a diluent, and examples thereof include a phosphoric acid buffer solution with a pH of 7.4, and the like. The pharmaceutical composition may include other diluents or additives in addition to the buffer solution.

A method of preparing a carrier used in the aforementioned preparation and the preparation may be selected and performed as widely known in the art, and the carrier and the preparation may be prepared according to the methods described in, for example, the Remington's Pharmaceutical Science latest edition.

The dosage and administration time of the pharmaceutical composition according to the present invention may vary depending on age, sex, status, and body weight of an administration subject, administration route, administration frequency, and type of drug. The daily dosage is about 0.1 mg/kg to about 1.000 mg/kg, preferably 1 mg/kg to 100 mg/kg. The dosage may be appropriately increased and decreased according to a type of disease, progress of disease, administration route, sex, age, body weight and the like.

In order to obtain a target effect, the pharmaceutical composition according to the present invention may be arbitrarily administered several times such that the total daily dosage as an effective ingredient is 0.1 mg/kg to 1,000 mg/kg as a compound based on an adult. The dosage may be appropriately increased and decreased according to a type of disease to be treated or prevented, progress of disease, administration route, sex, age, body weight, health status, and the like.

The pharmaceutical composition according to the present invention may contain the compound of Chemical Formula 1 or the compound of Chemical Formula 2 according to the present invention in an amount of about 0.0001 wt % to about 10 wt %, preferably 0.001 wt % to 1 wt % based on a total weight of the entire composition.

Hereinafter, one or more specific examples will be described in more detail through Examples. However, these Examples are provided only for exemplarily explaining one or more specific examples, and the scope of the present invention is not limited by these Examples.

Example 1: Preparation of (R)-3-(2-hydroxy-4-ethoxyphenyl)-8,8-dimethyl-2,3,4,8,9,10-hexahydropyrano[2,3-f]chromene (Compound 2a) and (S)-3-(2-hydroxy-4-ethoxyphenyl)-8,8-dimethyl-2,3,4,8,9,10-hexahydropyrano[2,3-f]chromene (Compound 2b)

3-(2-hydroxy-4-ethoxyphenyl)-8,8-dimethyl-2,3,4,8,9,10-hexahydropyrano[2,3-f]chromene in the form of a racemic compound was synthesized in accordance with the method exemplified in Korean Patent Application Laid-Open No. 10-2015-0075030 (Patent Document 2).

1-1: Preparation of 2-(2-benzyloxy-4-ethoxyphenyl)-3-(2,2-dimethyl-5-hydroxy-2H-1-benzopyran-6-yl)-acrylic acid methyl ester A three-neck round flask was cooled in a dry ice-acetone bath at −78° C. while being maintained under a nitrogen atmosphere, and 45 ml of a 1.0 M lithium diisopropyl amide (LDA)-THF solution was added thereto. Thereafter, 8.10 g (30.0 mmol) of (2-benzyloxy-4-ethoxyphenyl)acetic acid methyl ester was dissolved in 150 ml of THF and then the resulting solution was slowly added to the 1.0 M LDA-THF solution prepared above for 30 minutes, and the resulting mixture was additionally stirred for 30 minutes. Next, 9.24 g (30.0 mmol) of 5-benzoyloxy-2,2-dimethyl-6-formyl-2H-1-benzopyran was dissolved in 20 ml of THF, and then the solution was slowly added to the reaction solution prepared above over 30 minutes, and the resulting mixture was additionally stirred for 30 minutes. The round flask was separated from the dry ice-acetone bath, and then left to stand, and the reaction solution was slowly cooled at 0° C. In this state, 100 ml of brine was added thereto, the mixture was vigorously stirred at room temperature for 30 minutes, and then the organic layer was separated, and the aqueous layer was extracted one more time with 20 ml of ethyl acetate (CH₃COOC₂H). The organic layer extracted with ethyl acetate was combined with the organic layer previously separated, and the combined organic layer was dried over anhydrous magnesium sulfate, and then was concentrated by being distilled under reduced pressure. The concentrated solution was purified with silica gel column chromatography to obtain 5.79 g (12.70 mmol) of 2-(2-benzyloxy-4-ethoxyphenyl)-3-(2,2-dimethyl-5-hydroxy-2H-1-benzopyran-6-yl) acrylic acid methyl ester (Yield: 42.3%).

1-2: Preparation of 2-(2-benzyloxy-4-ethoxyphenyl)-3-(2,2-dimethyl-5-hydroxy-2H-1-benzopyran-6-yl)-propan-1-ol 4.56 g (10.0 mmol) of the 2-(2-benzyloxy-4-ethoxyphenyl)-3-(2,2-dimethyl-5-hydroxy-2H-1-benzopyran-6-yl)-acrylic acid methyl ester obtained in Example 1-1 was dissolved in 20 ml of THF, 60 ml of a 1.0 M THF solution of LiBH₄ was added thereto, and the resulting mixture was refluxed for 5 hours. The reaction solution was cooled in an ice bath, and then 50 ml of 1 N HCl was slowly added thereto, and extraction was performed by using 100 ml of CH 2. The organic layer was dried over anhydrous magnesium sulfate, and then was concentrated by being distilled under reduced pressure, and then the concentrated solution was purified with silica gel column chromatography to obtain 2.35 g (5.47 mmol) of 2-(2-benzyloxy-4-ethoxyphenyl)-3-(2,2-dimethyl-5-hydroxy-2H-1-benzopyran-6-yl)-propan-1-ol (Yield: 54.7%).

1-3: Preparation of 3-(2-benzyloxy-4-ethoxyphenyl)-8,8-dimethyl-2,3,4,8-tetrahydropyrano[2,3-f]chromen 1.57 g (3.65 mmol) of the 2-(2-benzyloxy-4-ethoxyphenyl)-3-(2,2-dimethyl-5-hydroxy-2H-1-benzopyran-6-yl)-propan-1-ol obtained in Example 1-2 was dissolved in 10 ml of THF, 0.995 g (3.80 mmol) of triphenylphosphine (Ph₃P) was added to the solution, and the reaction solution was slowly refluxed while being heated. While maintaining this state, 3.9 ml of a 1.0 M toluene solution of diethylazodicarboxylate (DEAD) was slowly added thereto, and the resulting mixture was vigorously stirred for 1 hour. The reaction solution was cooled to room temperature, and then concentrated by being distilled under reduced pressure, and the concentrated solution was purified with silica gel column chromatography to obtain 1.31 g (3.17 mmol) of 3-(2-benzyloxy-4-ethoxyphenyl)-8,8-dimethyl-2,3,4,8-tetrahydropyrano[2,3-f]chromene (Yield: 86.8%).

1-4: Preparation of 3-(2-hydroxy-4-ethoxyphenyl)-8,8-dimethyl-2,3,4,8,9,10-hexahydropyrano[2,3-f]chromen 4.12 g (10.0 mmol) of the 3-(2-benzyloxy-4-ethoxyphenyl)-8,8-dimethyl-2,3,4,8-tetrahydropyrano[2,3-f]chromene obtained in Example 1-3 was put into a 100-ml pressure vessel, 50 ml of ethanol was added thereto, and the resulting mixture was dissolved well. Thereafter, 150 mg of 5% palladium on carbon (Pd/C) was mixed with the solution, and the resulting mixture was vigorously stirred at room temperature for 25 hours while maintaining a hydrogen state of 5 atm. The reaction solution was filtered to remove the catalyst, and then concentrated by being distilled under reduced pressure, and the concentrated solution was purified with silica gel column chromatography to obtain 2.67 g (8.23 mmol) of 3-(2-hydroxy-4-ethoxyphenyl)-8,8-dimethyl-2,3,4,8,9,10-hexahydropyrano[2,3-f]chromene (Yield=82%).

1-5: Preparation of Optical Isomer of 3-(2-hydroxy-4-ethoxyphenyl)-8,8-dimethyl-2,3,4,8,9,10-hexahydropyrano[2,3-f]chromene The racemic compound obtained in Example 1-4 was separated into each isomer by column chromatography, and the column chromatography conditions are shown in the following Table 1.

TABLE 1

| | Conditions |
|---|---|
| Column | CHIRALPAK IA(Daicel) |
| | 0.46 cm I.D. × 25 cm L |
| Volume of sample injected | 2.0 μl |
| Sample solution | 1.0 mg/ml in Ethanol |
| Mobile phase | Hexane/Isopropanol = 95/5 (V/V) |
| Flow rate | 1.0 ml/min |
| Wavelength | UV 214 nm |
| Temperature | 35° C. |

FIG. 1 is a column chromatogram of optically active pyranochromenylphenol compounds 2a and 2b prepared in Example 1-4.

For comparison, an R-enantiomer was synthesized from glabridin (Daechon Chemical Co., Ltd., Korea), and then a result was obtained by carrying out column chromatography under the same conditions.

Figure 2:
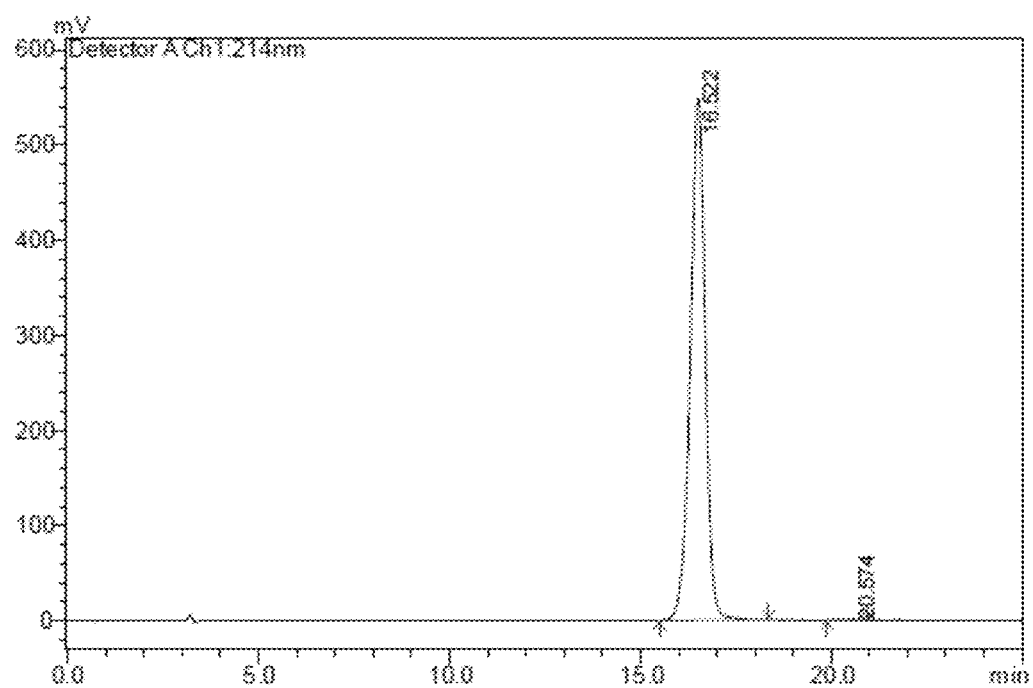
FIG. 2 is a column chromatogram of an R-enantiomer (Compound 2a) of a pyranochromenylphenol compound synthesized from glabridin.

FIG. 2 is a column chromatogram of an R-enantiomer (Compound 2a) of a pyranochromenylphenol compound synthesized from glabridin.

As a result of comparing the chromatogram of FIG. 2 with the chromatogram of FIG. 1, it could be seen that in FIG. 1, the peak in the 16.5 minute range is an R-enantiomer and the peak in the 20.5 minute range is an S-enantiomer.

The chromatography conditions for separating each of the R and S enantiomers from the racemic compound were confirmed, and then Daicel Chiral Technologies Co., Ltd. (China) was requested for the separation and purification of the racemic compound sample (37.0 g). As a result, 16.5 g of the R-enantiomer and 16.2 g of the S-enantiomer with >99% ee were obtained, and the results of ¹H-NMR, ¹³C-NMR, optical rotation, and melting point (M.P.) for the enantiomers are shown as follows.

¹H-NMR (CDCl₃): 6.995 (d, 1H, J=8.4 Hz), 6.832 (d, 1H, J=8.0 Hz), 6.465 (dd, 1H, J=8.0, 2.4 Hz), 6.388 (d, 1H, J=8.4 Hz), 6.331 (d, 1H, J=2.4 Hz), 5.170 (s, 1H), 4.389 (m, 1H, J=10.4, 3.2, 2.0 Hz), 4.009 (t, 1H, J=10.4 Hz), 3.960 (q, 2H, J=7.2 Hz), 3.483 (m, 1H), 3.010 (dd, 1H, J=15.6, 11.2 Hz), 2.858 (m, 1H, J=15.6, 4.8, 1.6 Hz), 2.642 (m, 2H), 1.773 (t, 2H, J=6.8 Hz), 1.384 (t, 2H, J=6.8 Hz), 1.333 (s, 3H), 1.318 (s, 3H).

¹³C-NMR (CDCl₃): 158.552, 154.340, 152.719, 152.091, 128.075, 127.465, 119.882, 112.909, 109.305, 109.248, 106.572, 102.504, 73.798, 70.018, 63.450, 32.311, 31.749, 30.614, 26.776, 26.390, 17.116, 14.781.

Optical Rotation Data
R-enantiomer—[α]$_D^{20}$: −6.2° (c=0.025, ethanol); and
S-enantiomer—[α]$_D^{20}$: +6.0° (c=0.025, ethanol).
M. P.
R-enantiomer: 132.5° C.; and
S-enantiomer: 132.0° C.

Example 2: Preparation of (R)-3-(2-hydroxy-4-propoxyphenyl)-8,8-dimethyl-2,3,4,8,9,10-hexahydropyrano[2,3-f]chromene (Compound 3a) and (S)-3-(2-hydroxy-4-propoxyphenyl)-8,8-dimethyl-2,3,4,8,9,10-hexahydropyrano[2,3-f]chromene (Compound 3b)

3-(2-hydroxy-4-propoxyphenyl)-8,8-dimethyl-2,3,4,8,9,10-hexahydropyrano[2,3-f]chromene was synthesized in the form of a racemic compound by using the same method as in Example 1, except that in Example 1-1, (2-benzyloxy-4-propoxyphenyl) acetic acid methyl ester was used instead of (2-benzyloxy-4-ethoxyphenyl) acetic acid methyl ester. Daicel Chiral Technologies Co., Ltd. was requested for the separation and purification of the synthesized sample, 10 g of an R-enantiomer and 10 g of an S-enantiomer with >99% ee were provided, and the results of $^1$H-NMR, $^{13}$C-NMR, optical rotation, and M.P. for the enantiomers are shown as follows.

$^1$H-NMR (CDCl$_3$): 6.976 (d, 1H, J=8.4 Hz), 6.817 (d, 1H, J=8.0 Hz), 6.452 (dd, 1H, J=8.0, 2.0 Hz), 6.392 (d, 1H, J=8.4 Hz), 6.316 (d, 1H, J=2.0 Hz), 5.600 (s, 1H), 4.380 (d, 1H, J=10.0 Hz), 4.000 (t, 1H, J=10.0 Hz), 3.812 (t, 2H, J=6.4 Hz), 3.488 (m, 1H), 2.997 (dd, 1H, J=15.6, 11.2 Hz), 2.837 (dd, 1H, J=15.6, 4.4 Hz), 2.640 (m, 2H), 1.782 (t, 2H, J=6.8 Hz), 1.765 (m, 2H), 1.329 (s, 3H), 1.314 (s, 3H), 0.994 (t, 3H, J=7.2 Hz).

$^{13}$C-NMR (CDCl$_3$): 158.678, 154.412, 152.596, 152.054, 128.015, 127.483, 119.827, 113.016, 109.299, 109.226, 106.588, 102.460, 73.888, 70.014, 69.537, 32.287, 31.702, 30.552, 26.728, 26.349, 22.453, 17.096, 10.458.

Optical Rotation Data
R-enantiomer—[α]$_D^{20}$: −5.3° (c=0.025, ethanol); and
S-enantiomer—[α]$_D^{20}$: +5.8° (c=0.025, ethanol).
M. P.
R-enantiomer: 153.6° C.; and
S-enantiomer: 153.4° C.

Example 3: Preparation of (R)-3-(2-hydroxy-4-butoxyphenyl)-8,8-dimethyl-2,3,4,8,9,10-hexahydropyrano[2,3-f]chromene (Compound 5a) and (S)-3-(2-hydroxy-4-butoxyphenyl)-8,8-dimethyl-2,3,4,8,9,10-hexahydropyrano[2,3-f]chromene (Compound 5b)

3-(2-hydroxy-4-butoxyphenyl)-8,8-dimethyl-2,3,4,8,9,10-hexahydropyrano[2,3-f]chromene was synthesized in the form of a racemic compound by using the same method as in Example 1, except that in Example 1-1, (2-benzyloxy-4-butoxyphenyl) acetic acid methyl ester was used instead of (2-benzyloxy-4-ethoxyphenyl) acetic acid methyl ester. Daicel Chiral Technologies Co., Ltd. was requested for the separation and purification of the synthesized sample, 10 g of an R-enantiomer and 10 g of an S-enantiomer with >99% ee were provided, and the results of $^1$H-NMR, $^{13}$C-NMR, optical rotation, and M.P. for the enantiomers are shown as follows.

$^1$H-NMR (CDCl$_3$): 7.009 (d, 1H, J=8.4 Hz), 6.847 (d, 1H, J=8.0 Hz), 6.482 (dd, 1H, J=8.0, 2.0 Hz), 6.408 (d, 1H, J=8.4 Hz), 6.355 (d, 1H, J=2.0 Hz), 5.313 (s, 1H), 4.407 (m, 1H, J=10.0 Hz), 4.027 (t, 1H, J=10.0 Hz), 3.906 (t, 2H, J=6.4 Hz), 3.503 (m, 1H), 3.027 (dd, 1H, J=15.6, 11.2 Hz), 2.874 (dd, 1H, J=15.6, 4.4 Hz), 2.662 (m, 2H), 1.70-1.90 (m, 4H), 1.482 (m, 2H), 1.351 (s, 3H), 1.337 (s, 3H), 0.977 (t, 3H, J=7.2 Hz).

$^{13}$C-NMR (CDCl$_3$): 158.793, 154.331, 152.721, 152.092, 128.047, 127.461, 119.777, 112.909, 109.299, 109.248, 106.628, 102.511, 73.786, 70.023, 67.738, 32.317, 31.756, 31.227, 30.626, 26.777, 26.390, 19.193, 17.117, 13.807.

Optical Rotation Data
R-enantiomer—[α]$_D^{20}$: −5.3° (c=0.025, ethanol); and
S-enantiomer—[α]$_D^{20}$: +5.1° (c=0.025, ethanol).
M. P.
R-enantiomer: 115.9° C.; and
S-enantiomer: 114.6° C.

Example 4: Preparation of (R)-3-(2-hydroxy-4-isopentyloxyphenyl)-8,8-dimethyl-2,3,4,8,9,10-hexahydropyrano[2,3-f]chromene (Compound 9a) and (S)-3-(2-hydroxy-4-isopentyloxyphenyl)-8,8-dimethyl-2,3,4,8,9,10-hexahydropyrano[2,3-f]chromene (Compound 9b)

3-(2-hydroxy-4-isopentyloxyphenyl)-8,8-dimethyl-2,3,4,8,9,10-hexahydropyrano[2,3-f]chromene was synthesized in the form of a racemic compound by using the same method as in Example 1, except that in Example 1-1, (2-benzyloxy-4-isopentyloxyphenyl) acetic acid methyl ester was used instead of (2-benzyloxy-4-ethoxyphenyl) acetic acid methyl ester.

Daicel Chiral Technologies Co., Ltd. was requested for the separation and purification of the synthesized sample, 0.5 g of an R-enantiomer and 0.5 g of an S-enantiomer with >99% ee were provided, and the results of $^1$H-NMR, $^{13}$C-NMR, M.P., and optical rotation for the enantiomers are shown as follows.

$^1$H-NMR (CDCl$_3$): 6.992 (d, 1H, J=8.4 Hz), 6.827 (d, 1H, J=8.4 Hz), 6.468 (dd, 1H, J=8.4, 2.0 Hz), 6.385 (d, 1H, J=8.4 Hz), 6.335 (d, 1H, J=2.0 Hz), 5.083 (s, 1H), 4.387 (m, 1H, J=10.0, 5.6, 2.4 Hz), 4.011 (t, 1H, J=10.0 Hz), 3.918 (t, 2H, J=6.8 Hz), 3.485 (m, 1H), 3.008 (dd, 1H, J=15.6, 11.2 Hz), 2.857 (dd, 1H, J=15.6, 4.4 Hz), 2.643 (m, 2H), 1.806 (m, 1H), 1.772 (t, 2H, J=6.8 Hz), 1.644 (m, 2H), 1.331 (s, 3H), 1.316 (s, 3H), 0.944 (t, 3H, J=6.4 Hz).

$^{13}$C-NMR (CDCl$_3$): 158.881, 154.197, 152.861, 152.137, 128.120, 127.459, 119.736, 112.789, 109.288, 109.284, 106.724, 102.561, 73.700, 70.031, 66.431, 37.940, 32.345, 31.805, 30.710, 26.836, 26.434, 25.031, 22.573, 17.150.

Optical Rotation Data
R-enantiomer—[α]$_D^{20}$: −1.7° (c=0.00, methylene chloride)
S-enantiomer—[α]$_D^{20}$: +1.5° (c=0.001, methylene chloride)
M. P.
R-enantiomer: 164.7° C.; and
S-enantiomer: 164.1° C.

Experimental Example 1: Anti-Obesity Effect Experiment of R-Enantiomer (Compound 2a) and S-Enantiomer (Compound 2b) of Optically Active Pyranochromenylphenol Compound For the anti-obesity efficacy of the R-enantiomer (Compound 2a) and the S-enantiomer (Compound 2b) of the optically active pyranochromenylphenol compound prepared in Example 1, an experiment was performed as follows.

Specifically, a 5- to 6-week-old female C57BL/6J mouse (Jackson Lab., USA) were purchased and fed with only high-fat fodder for at least 11 weeks to produce a diet induced obesity (DIO) mouse. Samples were exactly taken from a control and the racemic compound, the R-enantiomer (Compound 2a) and the S-enantiomer (Compound 2b) in Example 1 according to the administration dose (0, 20, and 50 mg/kg) and put into Falcon tubes, 3 ml of a 0.5% aqueous methyl cellulose solution was added thereto, and the resulting mixture was gently mixed by means of a vortex mixer. Thereafter, the mixture was homogenized by using a homogenizer (30,000 rpm, Ultra-Turrax® T10 Basic, IKA) for 3 minutes while 1.5 ml of a 0.5% aqueous methyl cellulose solution was added thereto. The sample thus prepared was administered through the oral gavage once daily for 6 weeks by using a disposable plastic syringe. The body weight was measured once a week while the DIO mouse was bred in this manner.

Based on the data thus measured, the anti-obesity effect was calculated according to the following Equation 1.

Anti-obesity effect (%)={(Body weight after compound is administered)−(Body weight before compound is administered)}/(Body weight before compound is administered))×100    [Equation 1]

As a result, as shown in the following Table 2, it could be confirmed that in the optically active pyranochromenylphenol compounds. Compound 2b being the S-enantiomer had a better effect of suppressing an increase in body weight than the racemic compound and Compound 2a being the R-enantiomer, and thus had an excellent anti-obesity activity.

TABLE 2

| Experimental group | Control (DIO mouse) | Racemic compound | | R-enantiomer (Compound 2a) | S-enantiomer (Compound 2b) |
|---|---|---|---|---|---|
| Administration dose (mg/kg) | 0 | 20 | 50 | 50 | 50 |
| Anti-obesity effect (%) | 35.02 | 16.11 | 2.29 | 7.58 | −10.99 |

Figure 3:
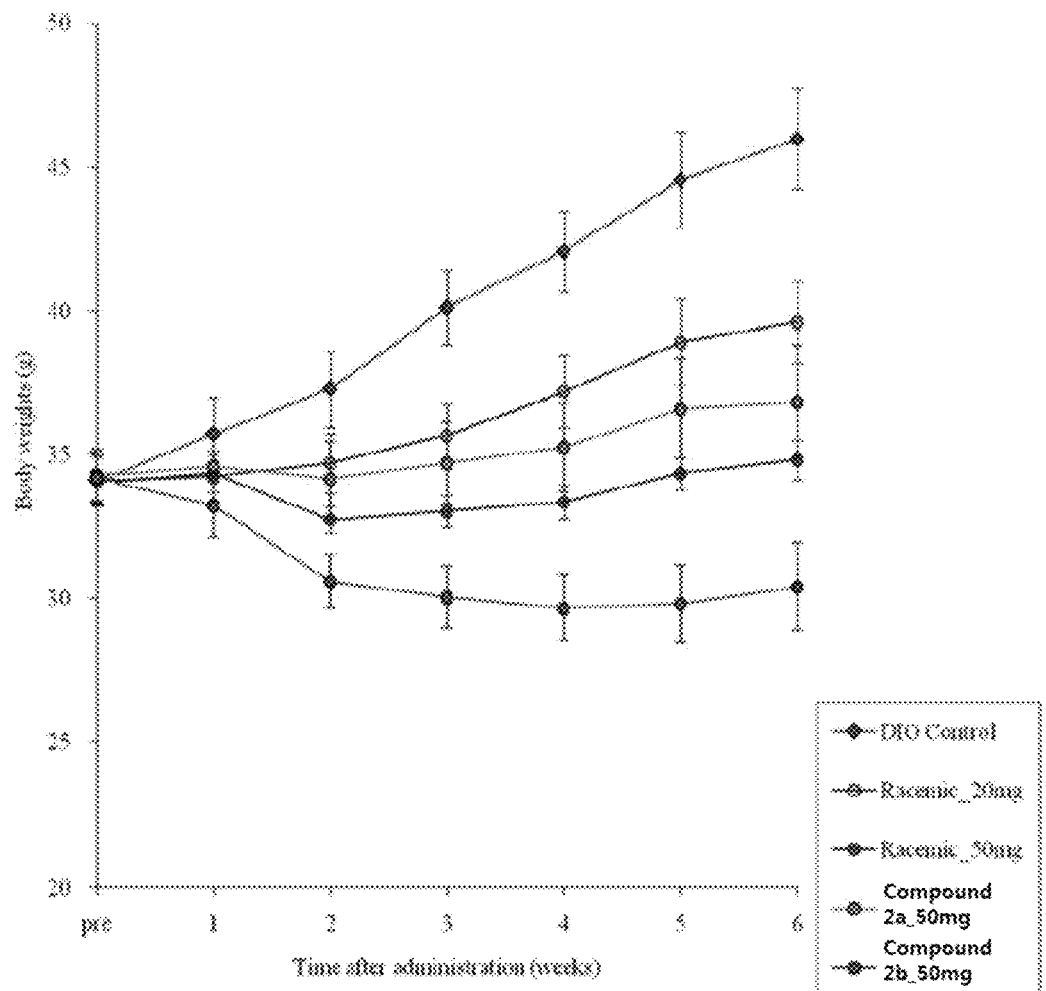
FIG. 3 is a graph illustrating the degree to which the body weight of a DIO mouse is increased according to the administration dose and administration period of a racemic compound of Compound 2 prepared in Example 1 of the present invention, Compound 2a, which is an R-enantiomer of Compound 2 prepared in Example 1 of the present invention, and Compound 2b, which is an S-enantiomer of Compound 2 prepared in Example 1 of the present invention.

FIG. 3 is a graph illustrating the degree to which the body weight of the DIO mouse is increased according to the administration dose and administration period of a racemic compound prepared in Example 1, and Compound 2a, which is an R-enantiomer prepared in Example 1, and Compound 2b, which is an S-enantiomer prepared in Example 1.

Experimental Example 2: Anti-Obesity Effect Experiment of R-Enantiomer (Compound 3a) and S-Enantiomer (Compound 3b) of Optically Active Pyranochromenylphenol Compound For the anti-obesity efficacy of the R-enantiomer (Compound 3a) and the S-enantiomer (Compound 3b) of the optically active pyranochromenylphenol compound prepared in Example 2, an experiment was performed in the same manner as in Experimental Example 1.

Based on the data thus measured, the anti-obesity effect was calculated according to Equation 1.

As a result, as shown in the following Table 3, it could be confirmed that in the optically active pyranochromenylphenol compounds according to the present invention, Compound 3b being the S-enantiomer had a better anti-obesity activity than Compound 3a being the R-enantiomer.

TABLE 3

| Experimental group | Control (DIO mouse) | R-enantiomer (Compound 3a) | S-enantiomer (Compound 3b) |
|---|---|---|---|
| Administration dose (mg/kg) | 0 | 200 | 200 |
| Anti-obesity effect (%) | 6.4 | −8.1 | −19.5 |

Figure 4:
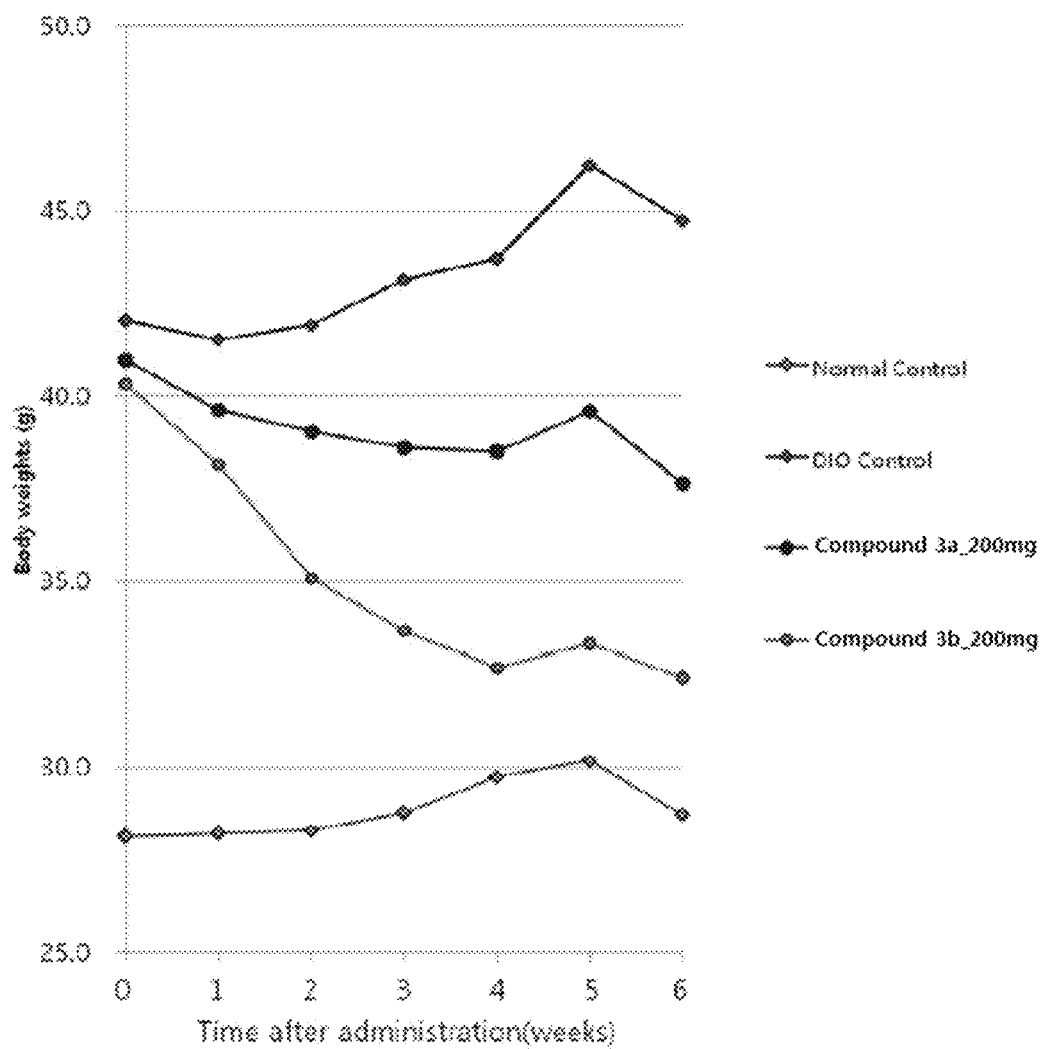
FIG. 4 is a graph illustrating the degree to which the body weight of a DIO mouse is increased according to the administration period of Compound 3a, which is an R-enantiomer of Compound 3 prepared in Example 2 of the present invention, and Compound 3b, which is an S-enantiomer of Compound 3 prepared in Example 2 of the present invention.

FIG. 4 is a graph illustrating the degree to which the body weight of the mouse is increased according to the administration period of Compound 3a being an R-enantiomer and Compound 3b being an S-enantiomer, which are prepared in Example 2 of the present invention.

As illustrated in FIG. 4, it can be seen that Compound 3b being the S-enantiomer has a better anti-obesity activity than Compound 3a being the R-enantiomer, and the body weight of the mouse administered with the S-enantiomer (Compound 3b) for 6 weeks has an excellent anti-obesity activity to such an extent as to be close to the body weight of the normal mouse.

Experimental Example 3: Anti-Diabetes Effect Experiment of R-Enantiomer (Compound 3a) and S-Enantiomer (Compound 3b) of Optically Active Pyranochromenylphenol Compound For the anti-diabetes efficacy of the R-enantiomer and the S-enantiomer of the optically active pyranochromenylphenol compound prepared in Example 2, an experiment was performed as follows.

Specifically, 5-week-old male C57BLKS/J-db/db mice (Central Lab. Animal Inc., Korea) were purchased and acclimatized for 2 weeks, and then used in the present experiment. The R-enantiomer (Compound 3a) and the S-enantiomer (Compound 3b) prepared in Example 2 were weighed (CP423S, Sartorius, Germany) according to the administration dose and put into 50 ml tubes, an excipient (10% LM 2125 CS MCT solution) stored at room temperature was added thereto, and then the resulting mixture was stirred by means of a vortex mixer so as to dissolve the excipient. Thereafter, the solution was ultrasonically treated for about 10 minutes, and a stock solution was prepared by formulating the solution at a predetermined concentration. A 0.5% aqueous MC solution as an excipient was added to the prepared stock solution, the resulting mixture was gently stirred by means of a vortex mixer, homogenized and prepared by means of a homogenizer (PT-1600E, Kinematica, Switzerland) at 30,000 rpm for 3 minutes, and then a solution was prepared at a final predetermined concentration by performing ultrasonic wave treatment for 30 minutes. The sample thus prepared was administered through the oral gavage once daily for 6 weeks by using a disposable plastic syringe with a zonde for oral administration attached.

While the C57BLKS/J-db/db mouse was bred, the mouse was fasted for 14 to 16 hours on the 48th day after administration, and then a glucose tolerance test was performed by orally administering glucose (Lot No: SLBM9269V, Sigma-Aldrich. USA) at a dose of 2 g/kg to the mice. Specifically, blood was collected from the caudal vein seven times in total including before the administration of glucose, at 15 minutes after the administration of glucose, at 30 minutes after the administration of glucose, at 60 minutes after the administration of glucose, at 120 minutes after the administration of glucose, at 180 minutes after the administration of glucose, and at 240 minutes after the administration of glucose. Thereafter, blood sugar was measured by using two blood sugar meters (AGM-4000, Allmedicus Inc., Korea), and then an average blood sugar was calculated by using each blood sugar measurement value. The area under the blood concentration-time curve (AUC) for the blood sugar value at each measurement time point was calculated by using a Phoenix WinNonlin program.

As a result, as shown in the following Table 4, it could be seen that in the pyranochromenylphenol derivatives according to the present invention, the R-enantiomer (Compound 3a) adjusted blood sugar well as compared to the S-enantiomer (Compound 3b).

TABLE 4

| Group | | Blood sugar (mg/dl) Time after administration of glucose (min) | | | | | | | AUC (mg/dl/ min) |
|---|---|---|---|---|---|---|---|---|---|
| | | 0 | 15 | 30 | 60 | 120 | 180 | 240 | |
| Negative control (0 mg/kg) | Average (mean) | 321 | 636 | 595 | 634 | 442 | 414 | 349 | 764 |
| | Standard deviation (S.D.) | 218 | 148 | 120 | 103 | 246 | 309 | 270 | 279 |
| | Standard error (S.E.) | 97 | 66 | 54 | 46 | 110 | 138 | 121 | 125 |
| | Number of samples (number) | 5 | 5 | 5 | 5 | 5 | 5 | 5 | 5 |
| R-enantiomer-Compound 3 a (100 mg/kg) | Average | 193 | 473 | 527 | 541 | 200 | 176 | 184 | 526 |
| | Standard deviation | 38 | 50 | 109 | 44 | 19 | 22 | 45 | 59 |
| | Standard error | 19 | 25 | 54 | 22 | 9 | 11 | 23 | 29 |
| | Number of samples | 4 | 4 | 4 | 4 | 4 | 4 | 4 | 4 |
| R-enantiomer-Compound 3 a (150 mg/kg) | Average | 175 | 440 | 469 | 460 | 234 | 153 | 163 | 481 |
| | Standard deviation | 25 | 43 | 74 | 94 | 26 | 20 | 18 | 55 |
| | Standard error | 11 | 19 | 33 | 42 | 12 | 9 | 8 | 24 |
| | Number of samples | 5 | 5 | 5 | 5 | 5 | 5 | 5 | 5 |
| R-enantiomer-Compound 3 a (200 mg/kg) | Average | 159 | 488 | 507 | 437 | 223 | 183 | 174 | 501 |
| | Standard deviation | 37 | 131 | 82 | 46 | 51 | 68 | 42 | 89 |
| | Standard error | 16 | 59 | 37 | 21 | 23 | 30 | 19 | 40 |
| | Number of samples | 5 | 5 | 5 | 5 | 5 | 5 | 5 | 5 |
| S-enantiomer-Compound 3 b (100 mg/kg) | Average | 392 | 595 | 616 | 628 | 472 | 422 | 397 | 782 |
| | Standard deviation | 215 | 185 | 110 | 150 | 227 | 298 | 231 | 292 |
| | Standard error | 96 | 83 | 49 | 67 | 101 | 133 | 103 | 130 |
| | Number of samples | 5 | 5 | 5 | 5 | 5 | 5 | 5 | 5 |

Experimental Example 4: Comparison of Anti-Diabetes Efficacies

By using the same method as in Experimental Example 3, a racemic compound of Compound 1, Compound 1a being an R-enantiomer, a racemic compound of Compound 3 prepared in Example 2 and Compound 3a being an R-enantiomer were administered to the C57BLKS/J-db/db mice, and then the anti-diabetes effects were confirmed.

Figure 5:
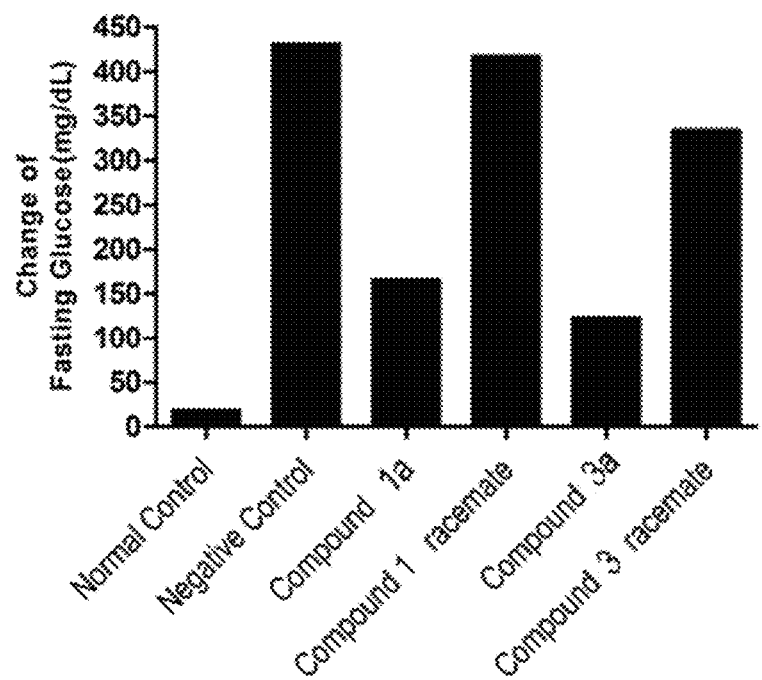
FIG. 5 is a graph illustrating the measurement results of a change in blood sugar of a db/db mouse according to the administration of a racemic compound (racemate) of Compound 1, Compound 1a, which is an R-enantiomer of Compound 1, and a racemic compound of Compound 3, and Compound 3a, which is an R-enantiomer of Compound 3.

FIG. 5 is a graph illustrating the measurement results of a change in blood sugar of a db/db mouse according to the administration of the racemic compound of Compound 1, Compound 1a, which is an R-enantiomer of Compound 1, the racemic compound of Compound 3 prepared in Example 2, and Compound 3a, which is an R-enantiomer of Compound 3.

As a result of observing the concentration of blood sugar in blood, as illustrated in FIG. 5, it could be seen that in the optically active pyranochromenylphenol derivatives according to the present invention, the R-enantiomer had excellent ability to adjust blood sugar as compared to the racemic compound.

The following Table 5 is a result of measuring a change in glycated hemoglobin of the db/db mouse according to the administration of the normal group, the negative control the racemic compound of Compound 1, Compound 1a being the R-enantiomer, the racemic Compound of Compound 3 prepared in Example 2 and Compound 3a being the R-enantiomer.

TABLE 5

| | | Glycated hemoglobin (HbA1c, %) | | |
|---|---|---|---|---|
| Group | | Before administration | 29th day after administration | 43rd day after administration |
| Normal group (0 mg/kg) | Average | 4.2 | 4.1 | 4.2 |
| | Standard deviation | 0.2 | 0.1 | 0.2 |
| | Number of samples | 4 | 4 | 4 |
| Negative control (0 mg/kg) | Average | 4.7 | 9.2 | 9.0 |
| | Standard deviation | 0.4 | 1.7 | 1.8 |
| | Number of samples | 5 | 5 | 5 |
| R-enantiomer-Compound 1a (300 mg/kg) | Average | 4.7 | 9.0 | 7.6 |
| | Standard deviation | 0.2 | 1.6 | 1.8 |
| | Number of samples | 7.0 | 7.0 | 7 |
| Racemic compound-Compound 1 (300 mg/kg) | Average | 4.7 | 10.6 | 9.7 |
| | Standard deviation | 0.3 | 1.4 | 2.4 |
| | Number of samples | 7.0 | 7.0 | 7.0 |
| R-enantiomer-Compound 3a (300 mg/kg) | Average | 4.7 | 7.1 | 5.3 |
| | Standard deviation | 0.3 | 1.5 | 1.0 |
| | Number of samples | 7.0 | 7.0 | 7.0 |
| Racemic compound-Compound 3 (300 mg/kg) | Average | 4.7 | 6.7 | 6.2 |
| | Standard deviation | 0.2 | 1.3 | 1.0 |
| | Number of samples | 7.0 | 7.0 | 7.0 |

Figure 6:
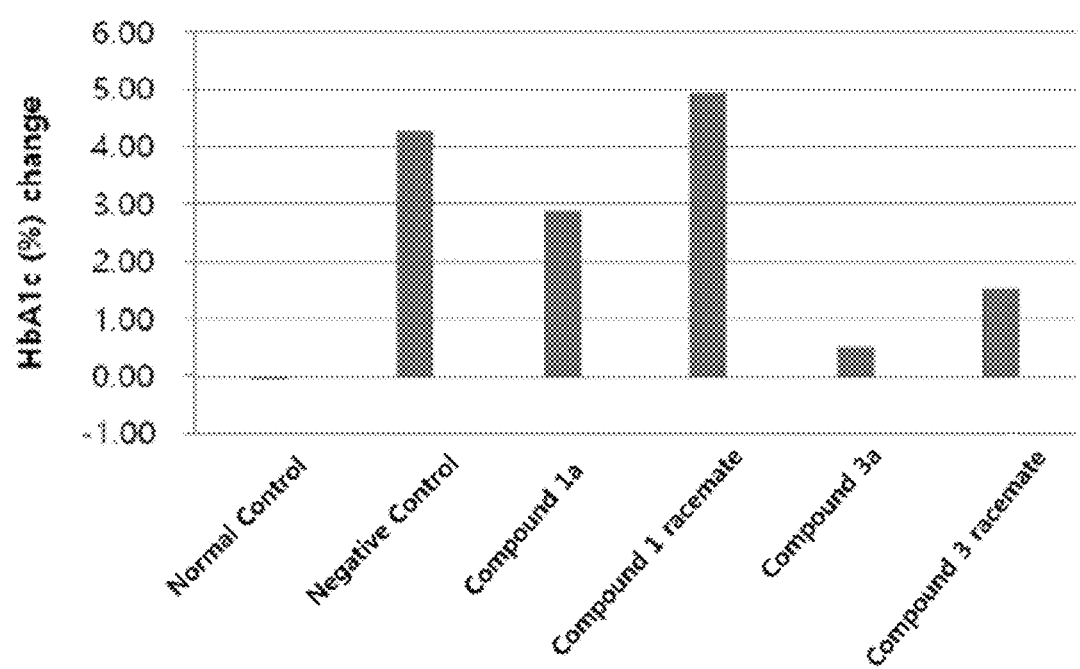
FIG. 6 is a graph illustrating a change in glycated hemoglobin of a db/db mouse according to the administration of a racemic compound of Compound 1, Compound 1a, which is an R-enantiomer of Compound 1, and a racemic compound of Compound 3, and Compound 3a, which is an R-enantiomer of Compound 3.

FIG. 6 is a graph illustrating a change in glycated hemoglobin of a db/db mouse according to the administration of a racemic compound of Compound 1, Compound 1a, which is an R-enantiomer of Compound 1, a racemic compound of Compound 3 prepared in Example 2, and Compound 3a, which is an R-enantiomer of Compound 3.

Figure 7:
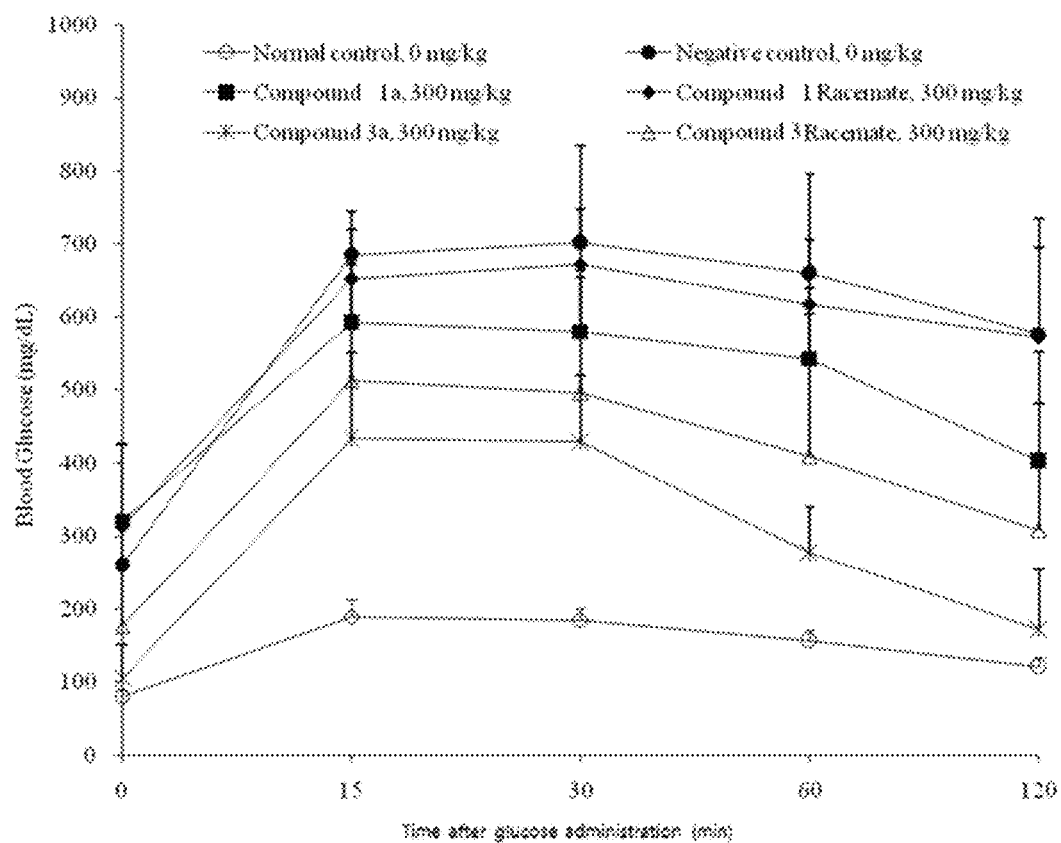
FIG. 7 is a graph illustrating the results of a glucose tolerance test of a db/db mouse administered with a racemic compound of Compound 1, Compound 11a, which is an R-enantiomer of Compound 1, a racemic compound of Compound 3, and Compound 3a, which is an R-enantiomer of Compound 3.

FIG. 7 is a graph illustrating the results of a glucose tolerance test of a db/db mouse administered with the racemic compound of Compound, Compound 1a, which is an R-enantiomer of Compound 1, the racemic compound of Compound 3 prepared in Example 2, and Compound 3a, which is an R-enantiomer of Compound 3.

As described above, it could be confirmed that the optically active pyranochromenylphenol derivative according to the present invention had better anti-obesity activity or anti-diabetes activity than the racemic compound, and it could be seen that the respective optical isomers had different activities.

Hitherto, the present invention has been reviewed mainly in the preferred examples thereof. A person with ordinary skill in the art to which the present invention pertains will be able to understand that the present invention may be implemented in a modified form without departing from the essential characteristics of the present invention. Therefore, the disclosed examples are to be considered not from a restrictive viewpoint, but from an explanatory viewpoint. It is to be interpreted that the scope of the present invention is described not in the above-described explanation, but in the claims, and all the differences within a range equivalent thereto are included in the present invention.

The invention claimed is:

1. A method for treating diabetes in a subject in need thereof, the method comprising administering to the subject a pyranochromenylphenol compound having the structure of Chemical Formula (I) or a pharmaceutically acceptable salt thereof:

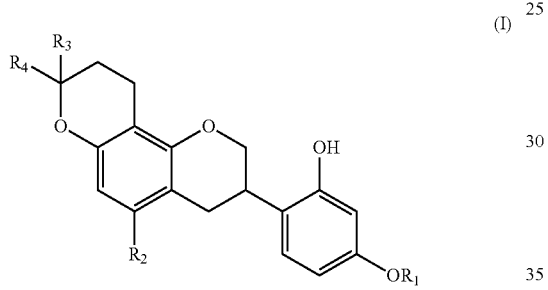

(I)

wherein the compound having the structure of Chemical Formula (I) is optically active due to enantiomeric enrichment with the (R) enantiomer, which is a compound of Chemical Formula (Ia) or a pharmaceutically acceptable salt thereof:

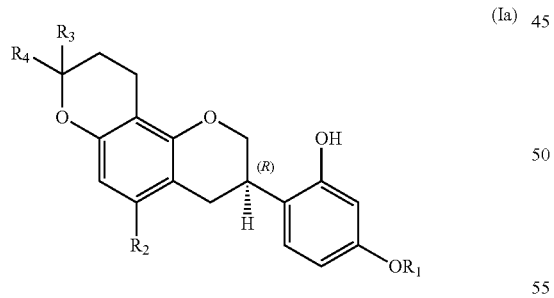

(Ia)

thereby treating the diabetes in the subject,
wherein:
$R_1$ is a straight or branched $C_1$ to $C_6$ alkyl group unsubstituted or substituted by a straight or branched $C_1$ to $C_5$ alkyl group, a halogen atom, or a $C_1$ to $C_5$ thioalkyl group;
$R_2$ is a hydrogen atom, methyl, ethyl, methoxy or ethoxy; and
$R_3$ and $R_4$ are each independently a hydrogen atom or a $C_1$ to $C_2$ alkyl group.

2. The method of claim 1,
wherein:
$R_1$ is methyl, ethyl, n-propyl, isopropyl, n-butyl, 2-methylpropyl, n-pentyl, 2-methylbutyl, 3-methylbutyl, 2-ethylpropyl, n-hexyl, 2-methylpentyl, 3-methylpentyl, 4-methylpentyl, or 2-ethylbutyl;
$R_2$ is a hydrogen atom; and
$R_3$ and $R_4$ are each methyl.

3. The method of claim 1,
wherein:
$R_1$ is methyl, ethyl, n-propyl, isopropyl, n-butyl, 2-methylpropyl, n-pentyl, 2-methylbutyl, 3-methylbutyl, 2-ethylpropyl, n-hexyl, 2-methylpentyl, 3-methylpentyl, 4-methylpentyl, or 2-ethylbutyl;
$R_2$ is methyl or methoxy; and
$R_3$ and $R_4$ are each methyl.

4. The method of claim 1,
wherein the compound of Chemical Formula (Ia) is any one of the following compounds:

<Compound 1a>

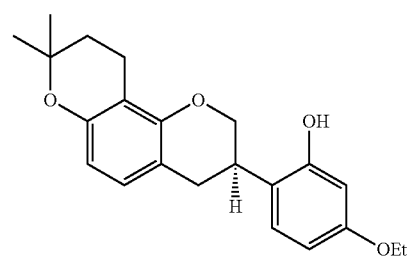

<Compound 2a>

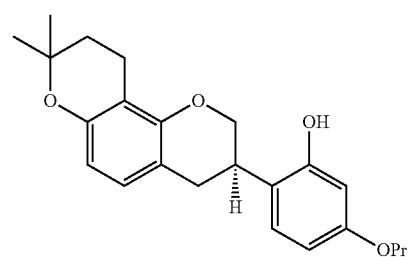

<Compound 3a>

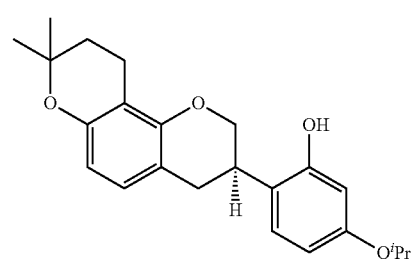

<Compound 4a>

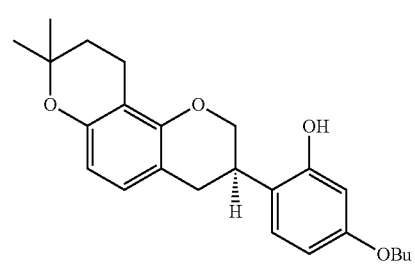

<Compound 5a>
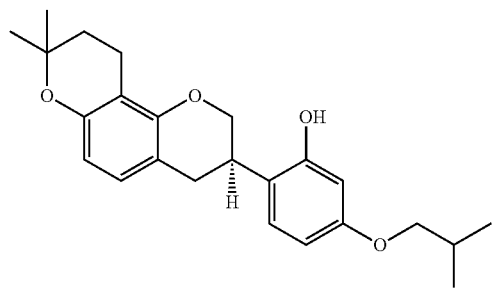
<Compound 6a>
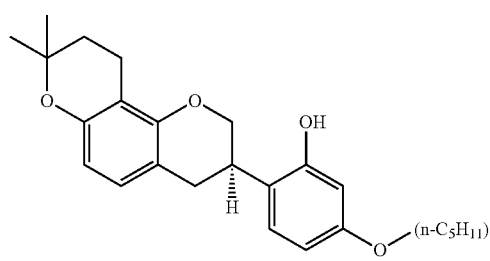
<Compound 7a>
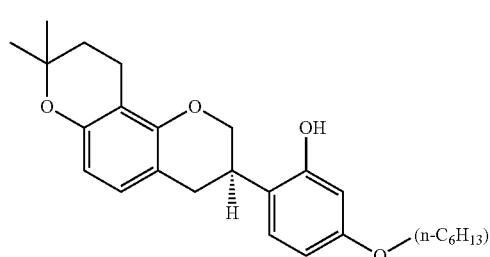
<Compound 8a>
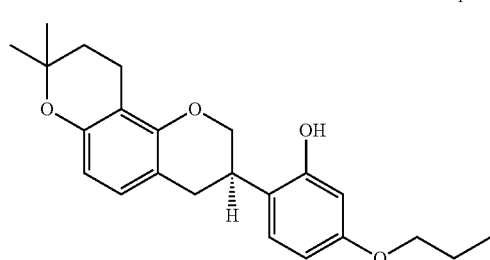
<Compound 9a>
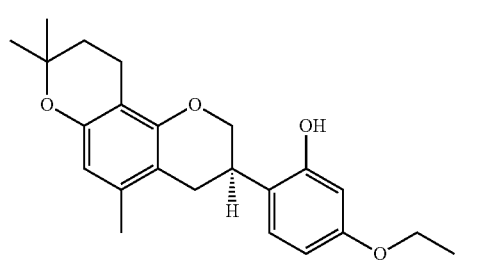
<Compound 10a>
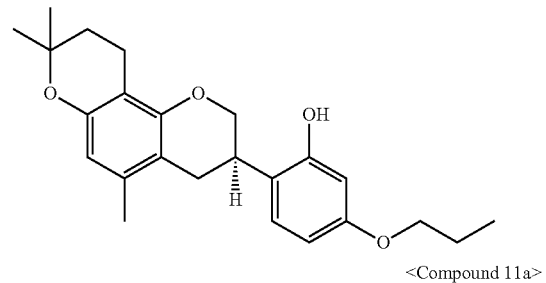
<Compound 11a>
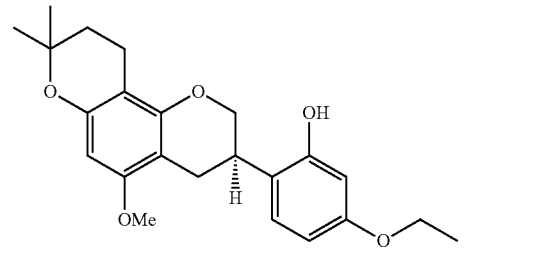
<Compound 12a>
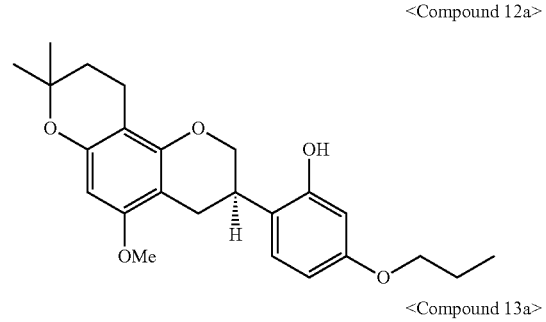
<Compound 13a>
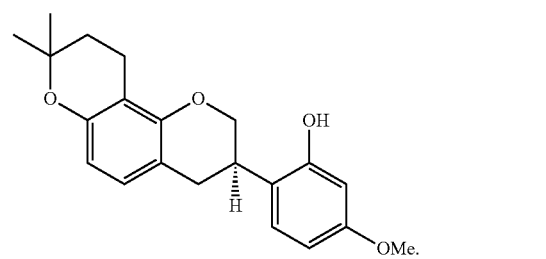
5. A method for treating obesity in a subject in need thereof, the method comprising administering to the subject a pyranochromenylphenol compound having the structure of Chemical Formula (I) or a pharmaceutically acceptable salt thereof:
(I)
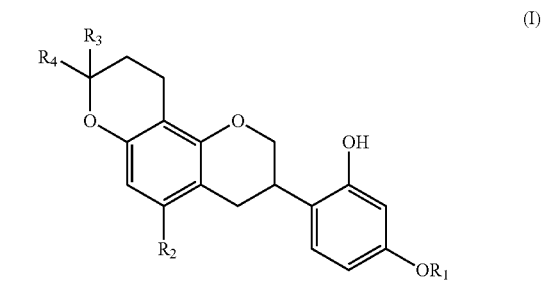

wherein the compound having the structure of Chemical Formula (I) is optically active due to enantiomeric enrichment with the (S) enantiomer, which is a compound of Chemical Formula (Ib), or a pharmaceutically acceptable salt thereof:

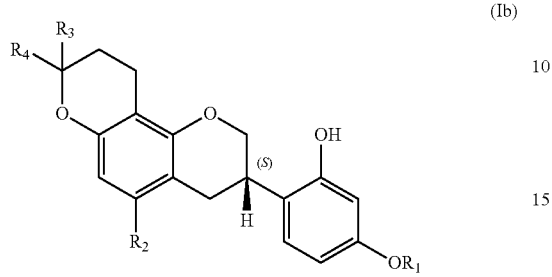

(Ib)

thereby treating the obesity in the subject, wherein:

$R_1$ is a straight or branched $C_1$ to $C_6$ alkyl group unsubstituted or substituted by a straight or branched $C_1$ to $C_5$ alkyl group, a halogen atom, or a $C_1$ to $C_5$ thioalkyl group;

$R_2$ is a hydrogen atom, methyl, ethyl, methoxy or ethoxy; and $R_3$ and $R_4$ are each independently a hydrogen atom or a $C_1$ to $C_2$ alkyl group.

6. The method of claim 5, wherein:

$R_1$ is methyl, ethyl, n-propyl, isopropyl, n-butyl, 2-methylpropyl, n-pentyl, 2-methylbutyl, 3-methylbutyl, 2-ethylpropyl, n-hexyl, 2-methylpentyl, 3-methylpentyl, 4-methylpentyl, and 2-ethylbutyl;

$R_2$ is a hydrogen atom; and $R_3$ and $R_4$ are each methyl.

7. The method of claim 5, wherein:

$R_1$ is methyl, ethyl, n-propyl, isopropyl, n-butyl, 2-methylpropyl, n-pentyl, 2-methylbutyl, 3-methylbutyl, 2-ethylpropyl, n-hexyl, 2-methylpentyl, 3-methylpentyl, 4-methylpentyl, and 2-ethylbutyl;

$R_2$ is methyl or methoxy; and $R_3$ and $R_4$ are each methyl.

8. The method of claim 5, wherein the compound of Chemical Formula (IIb) is any one of the following compounds:

<Compound 1b>

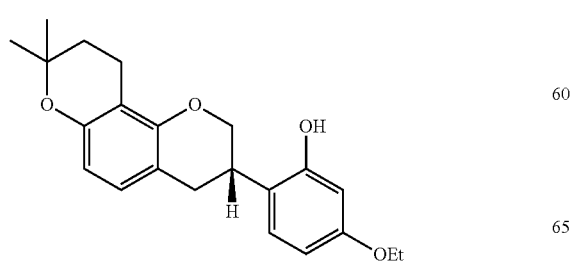

<Compound 2b>

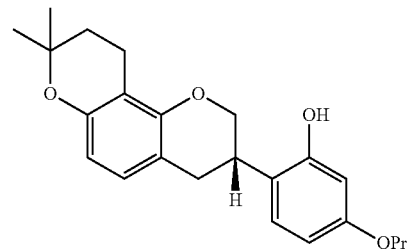

<Compound 3b>

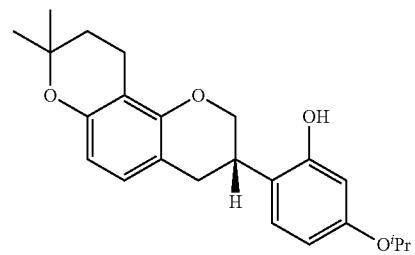

<Compound 4b>

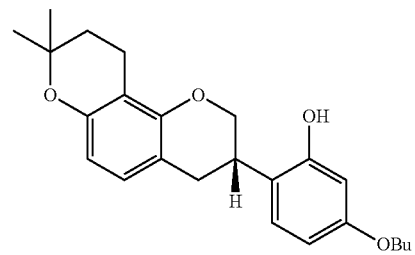

<Compound 5b>

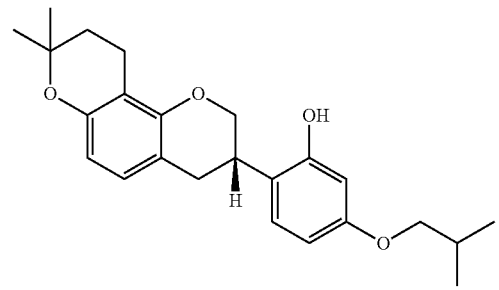

<Compound 6b>

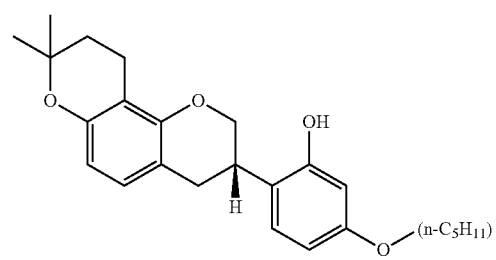

-continued

<Compound 7b>
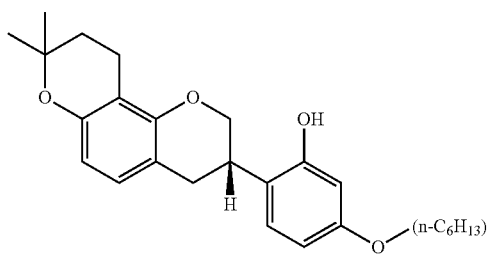

<Compound 8b>
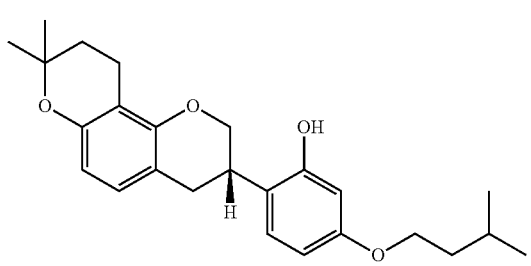

<Compound 9b>
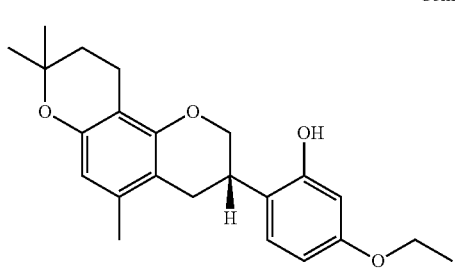

<Compound 10b>
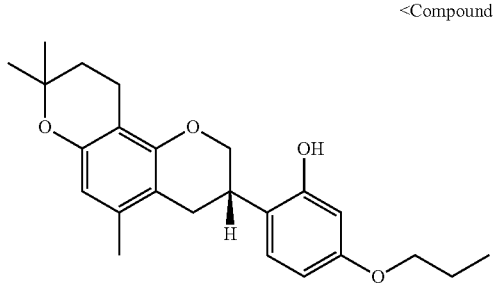

-continued

<Compound 11b>
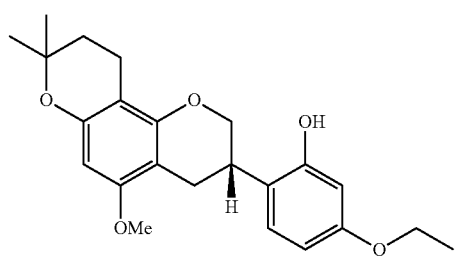

<Compound 12b>
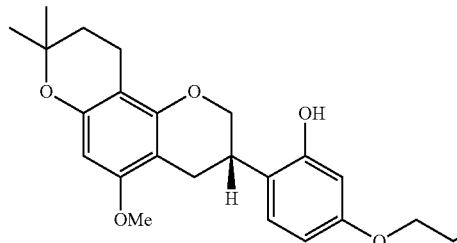

<Compound 13b>
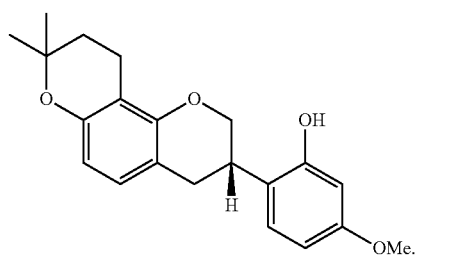

9. The method of claim 1, wherein the compound of Chemical Formula (I) has an enantiomeric excess (% ee) of greater than 99% with respect to the compound of Chemical Formula (Ia).

10. The method of claim 1, wherein the compound of Chemical Formula (I) treats the diabetes by adjusting a blood sugar level in the subject.

11. The method of claim 10, wherein adjusting a blood sugar level in the subject comprises lowering the blood sugar level in the subject.

12. The method of claim 5, wherein the compound of Chemical Formula (I) has an enantiomeric excess (% ee) of greater than 99% with respect to the compound of Chemical Formula (Ib).

13. The method of claim 5, wherein the compound of Chemical Formula (I) treats obesity by reducing body weight of the subject.

* * * * *